US008829217B2

(12) United States Patent
Fox et al.

(10) Patent No.: US 8,829,217 B2
(45) Date of Patent: Sep. 9, 2014

(54) METHODS OF FORMING SINGLE SOURCE PRECURSORS, METHODS OF FORMING POLYMERIC SINGLE SOURCE PRECURSORS, AND SINGLE SOURCE PRECURSORS FORMED BY SUCH METHODS

(71) Applicant: Battelle Energy Alliance, LLC, Idaho Falls, ID (US)

(72) Inventors: Robert V. Fox, Idaho Falls, ID (US); Rene G. Rodriguez, Pocatello, ID (US); Joshua J. Pak, Pocatello, ID (US); Chivin Sun, Pocatello, ID (US); Kelsey R. Margulieux, Pocatello, ID (US); Andrew W. Holland, Pocatello, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 13/659,620

(22) Filed: Oct. 24, 2012

(65) Prior Publication Data
US 2013/0060054 A1  Mar. 7, 2013

Related U.S. Application Data

(62) Division of application No. 12/646,474, filed on Dec. 23, 2009, now Pat. No. 8,324,414.

(51) Int. Cl.
*C07F 19/00* (2006.01)

(52) U.S. Cl.
CPC .................................. *C07F 19/005* (2013.01)
USPC ............................................. 556/14; 556/28

(58) Field of Classification Search
CPC ....................................................... C07F 19/005
USPC ....................................................... 556/14, 28
See application file for complete search history.

(56) References Cited

U.S. PATENT DOCUMENTS

| | | | |
|---|---|---|---|
| 4,155,781 A | 5/1979 | Diepers | |
| 4,687,881 A | 8/1987 | Goslowsky et al. | |
| 4,906,290 A | 3/1990 | Worner | |
| 5,445,847 A | 8/1995 | Wada et al. | |
| 5,501,786 A | 3/1996 | Gremion et al. | |
| 5,567,469 A | 10/1996 | Wada et al. | |
| 5,858,120 A | 1/1999 | Nakagawa et al. | |
| 6,127,202 A | 10/2000 | Kapur et al. | |
| 6,145,342 A | 11/2000 | Bayya et al. | |
| 6,284,314 B1 | 9/2001 | Kato et al. | |
| 6,307,148 B1 | 10/2001 | Takeuchi et al. | |
| 6,355,874 B1 | 3/2002 | Yagi et al. | |
| 6,429,369 B1 | 8/2002 | Tober et al. | |
| 6,592,938 B1 | 7/2003 | Pessey et al. | |
| 6,875,661 B2 | 4/2005 | Mitzi | |
| 6,992,201 B2 | 1/2006 | Scholz et al. | |
| 6,992,202 B1 | 1/2006 | Banger et al. | |
| 7,068,898 B2 | 6/2006 | Buretea et al. | |
| 7,265,037 B2 | 9/2007 | Yang et al. | |
| 7,351,282 B2 | 4/2008 | Yamaguchi | |
| 7,466,376 B2 | 12/2008 | Galvin et al. | |
| 7,545,051 B2 | 6/2009 | Yang et al. | |
| 7,575,699 B2 | 8/2009 | Strouse et al. | |
| 7,615,169 B2 | 11/2009 | Strouse et al. | |
| 7,883,799 B2 | 2/2011 | Seo et al. | |
| 7,892,519 B2 | 2/2011 | Pak et al. | |
| 8,003,070 B2 | 8/2011 | Fox et al. | |
| 2002/0005145 A1 | 1/2002 | Sherman | |
| 2002/0071970 A1 | 6/2002 | Elder et al. | |
| 2003/0226498 A1 | 12/2003 | Alivisatos et al. | |
| 2004/0031519 A1 | 2/2004 | Andriessen | |
| 2004/0095658 A1 | 5/2004 | Buretea et al. | |
| 2004/0120884 A1 | 6/2004 | Sherman | |
| 2004/0126485 A1 | 7/2004 | Thompson et al. | |
| 2004/0131934 A1 | 7/2004 | Sugnaux et al. | |
| 2004/0256001 A1 | 12/2004 | Mitra et al. | |
| 2005/0016577 A1 | 1/2005 | Andriessen et al. | |
| 2005/0133087 A1 | 6/2005 | Alivisatos et al. | |
| 2005/0183767 A1 | 8/2005 | Yu et al. | |
| 2005/0267345 A1 | 12/2005 | Korgel et al. | |
| 2005/0271827 A1 | 12/2005 | Krunks et al. | |
| 2006/0110314 A1 | 5/2006 | Torardi | |
| 2006/0110315 A1 | 5/2006 | Torardi | |
| 2006/0110316 A1 | 5/2006 | Torardi | |

(Continued)

FOREIGN PATENT DOCUMENTS

GB    2472541 B    3/2011

OTHER PUBLICATIONS

Qi et al., "Synthesis and Characterization of Nanostructured Wurtzite CuInS2: A New Cation Disordered Polymorph of CuInS2," J. Phys. Chem. C 2009, 113, 3939-3944.
Rodriguez et al., "The Formation of Copper Indium Disulfide Nano-Particles in Supercritical Carbon Dioxide," NORM 2007, American Chemical Society, The 62nd Northwest Regional Meeting, Boise, Idaho, Jun. 17-20, 2007, 5 pages.
Rodriguez, et al., "Pulsed-Spray Radiofrequency Plasma Enhanced Chemical Vapor Deposition of CUInS2 Thin Films," Plasma Chemistry and Plasma Processing, vol. 26, No. 2, Apr. 2006 , pp. 137-148.
Sayilkan et al., "Characterization of TiO2 Synthesized in Alcohol by a Sol-Gel Process: The Effects of Annealing Temperature and Acid Catalyst," Turk J Chem, 29 (2005) pp. 697-706.

(Continued)

*Primary Examiner* — Porfirio Nazario Gonzalez
(74) *Attorney, Agent, or Firm* — TraskBritt

(57) ABSTRACT

Methods of forming single source precursors (SSPs) include forming intermediate products having the empirical formula $½\{L_2N(μ-X)_2M'X_2\}_2$, and reacting MER with the intermediate products to form SSPs of the formula $L_2N(μ-ER)_2M'(ER)_2$, wherein L is a Lewis base, M is a Group IA atom, N is a Group IB atom, M' is a Group IIIB atom, each E is a Group VIB atom, each X is a Group VIIA atom or a nitrate group, and each R group is an alkyl, aryl, vinyl, (per)fluoro alkyl, (per)fluoro aryl, silane, or carbamato group. Methods of forming polymeric or copolymeric SSPs include reacting at least one of $HE^1R^1E^1H$ and MER with one or more substances having the empirical formula $L_2N(μ-ER)_2M'(ER)_2$ or $L_2N(μ-X)_2M'(X)_2$ to form a polymeric or copolymeric SSP. New SSPs and intermediate products are formed by such methods.

17 Claims, 3 Drawing Sheets

(56) References Cited

U.S. PATENT DOCUMENTS

| | | |
|---|---|---|
| 2006/0110317 A1 | 5/2006 | Torardi |
| 2006/0110318 A1 | 5/2006 | Torardi |
| 2006/0144793 A1 | 7/2006 | Dadachov |
| 2006/0159611 A1 | 7/2006 | Hummelen et al. |
| 2006/0216610 A1 | 9/2006 | Galvin et al. |
| 2006/0249373 A1 | 11/2006 | Vanderstraeten |
| 2006/0263291 A1 | 11/2006 | Torardi |
| 2007/0000537 A1 | 1/2007 | Leidholm et al. |
| 2007/0025139 A1 | 2/2007 | Parsons |
| 2007/0102040 A1 | 5/2007 | Beckenbaugh et al. |
| 2007/0204904 A1 | 9/2007 | Brooks et al. |
| 2007/0209700 A1 | 9/2007 | Yonezawa et al. |
| 2007/0277871 A1 | 12/2007 | Lee et al. |
| 2007/0295385 A1 | 12/2007 | Sheats et al. |
| 2008/0006322 A1 | 1/2008 | Wang et al. |
| 2008/0006324 A1 | 1/2008 | Berke et al. |
| 2008/0012015 A1 | 1/2008 | Shim et al. |
| 2008/0023677 A1 | 1/2008 | Frechet et al. |
| 2008/0026929 A1 | 1/2008 | Jensen et al. |
| 2008/0031832 A1 | 2/2008 | Wakefield et al. |
| 2008/0041447 A1 | 2/2008 | Tseng et al. |
| 2008/0110494 A1 | 5/2008 | Reddy |
| 2008/0142075 A1 | 6/2008 | Reddy et al. |
| 2008/0149171 A1 | 6/2008 | Lu et al. |
| 2008/0156371 A1 | 7/2008 | LoCascio et al. |
| 2008/0207581 A1 | 8/2008 | Whiteford et al. |
| 2008/0230120 A1 | 9/2008 | Reddy |
| 2008/0289681 A1 | 11/2008 | Adriani et al. |
| 2008/0289682 A1 | 11/2008 | Adriani et al. |
| 2008/0308148 A1 | 12/2008 | Leidholm et al. |
| 2009/0050207 A1 | 2/2009 | Galvin et al. |
| 2009/0133751 A1 | 5/2009 | Sreenivasan et al. |
| 2009/0173371 A1 | 7/2009 | Skoczenski et al. |
| 2009/0233398 A1 | 9/2009 | Fox et al. |
| 2011/0027572 A1 | 2/2011 | Wiesner |
| 2011/0152554 A1 | 6/2011 | Fox et al. |
| 2011/0204320 A1 | 8/2011 | Fox et al. |
| 2012/0108418 A1 | 5/2012 | Nair et al. |
| 2012/0192930 A1 | 8/2012 | Fox et al. |

OTHER PUBLICATIONS

Sobolev, N.A., et al., "Enhanced Radiation Hardness of InAs/GaAs quantum Dot Structures," Phys. Stat. Sol. (B), 2001, pp. 93-96, vol. 224, No. 1.

Sun et al., "A High-Yield Synthesis of Chalcopyrite CuInS2 Nanoparticles with Exceptional Size Control," Journal of Nanomaterials, vol. 2009, Article ID 748567, 7 pages.

Tang, Z., et al., "Semiconductor Nanoparticles on Solid Substrates: Film Structure, Intermolecular Interactions, and Polyelectrolyte Effects," Langmuir, 2002, pp. 7035-7740, vol. 18.

Tomalia, D.A., "Birth of a New Macromolecular Architecture: Dendrimers as Quantized Building Blocks for Nanoscale Synthetic Organic Chemistry," Aldrichimica ACTA, 2004, pp. 39-57, vol. 27, No. 2.

Vittal et al., "Chemistry of metal thio- and selenocarboxylates: precursors for metal sulfide/selenide materials, thin films, and nanocrystals," Acc. Chem. Res. (2006) 39:869-877.

Walters, R.J., et al., "Radiation Hard Multi-quantum Well InP/InAsP Solar Cells for Space Applications," Progress in Photovoltaics: Research and Applications, 2000, pp. 349-354, vol. 8.

Wang et al., "Synthesis of Monodispersed Wurtzite Structure CuInSe2 Nanocrystals and Their Application in High-Performance Organic-Inorganic Hybrid Photodetectors," J. Am. Chem. Soc., 2010, 132 (35), pp. 12218-12221.

Wang, Y., et al., "Nanometer-Sized Semiconductor Clusters: Materials Synthesis, Quantum Size Effects, and Photophysical Properties," J. Phys. Chem., 1991, pp. 525-532, vol. 95.

Wei, Q., et al., "Synthesis of CuInS(2) Nanocubes by a Wet Chemical Process," Journal of Dispersion Science and Technology, 2005, pp. 555-558, vol. 26.

Zhang, X., et al., "Applications of microwave dielectric heating in environment-related heterogeneous gas-phase catalytic systems," Inorganica Chimica Acta, 2006, pp. 3421-3433, vol. 359.

Zhu, J., et al., "Microwave assisted preparation of CdSe, PbSe, andCU2-x Se nanoparticles," J. Phys. Chem. B., 2000, 104 (31), 7344-7347.

Bahnemann, D. W., "Ultrasmall Metal Oxide Particles: Preparation, Photophysical Characterization, and Photocatalytic Properties". Israel J. Chem., 1993, pp. 115-136, vol. 33.

Bamba et al., "TiO2—ZnO Porous Films Formed by ZnO Dissolution," AZojomo, vol. 3, Dec. 2007, 7 pages.

Banger et al., "A review of single source precursors for the deposition of ternary chalcopyrite materials," NASA Conference Publication (2002), 17th Space Photovoltaic Research and Technology Conference, 2001, pp. 115-125.

Banger et al., "Ternary single-source precursors for polycrystalline thin-film solar cells," Appl. Organomet. Chem. (2002) 16:617-627.

Banger, K.K., et al., "A New Facile Route for the Preparation of Single-Source Precursors for Bulk, Thin-Film, and Nanocrystallite I-III-VI Semiconductors," Inorg. Chem., 2003, pp. 7713-7715, vol. 42, No. 24.

Banger, K.K., et al., "Facile modulation of single source precursors: the synthesis and characterization of single source precursors for deposition of ternary chalcopyrite materials," Thin Solid Films, 2002, pp. 390-395, vol. 403-404.

Banger, K.K., et al., "Synthesis and Characterization of the First Liquid Ssingle-Source Precursors for the Deposition of Ternary Chalcopyrite (CuInS(2)) Thin Film Materials," Chem. Mater., 2001, pp. 3827-3829, vol. 13.

Cardellicchio, N., et al., "Optimization of Microwave Digestion for Mercury Determination in Marine Biological Samples by Cold Vapour Atomic Absorption Spectrometry", Annali di Chimica, 2006, pp. 159-165, vol. 96 (3-4).

Carro, N., et al., "Microwave-assisted solvent extraction and gas chromatography ion trap mass spectrometry procedure for the determination of persistent organochlorine pesticides (POPs) in marine sediment", Anal. Bioanal. Chem., 2006, pp. 901-909, vol. 385.

Castro, S.L., et al., "Synthesis and Characterization of Colloidal CuInS(2) Nanoparticles from a Molecular Single-Source Precursor," J Phys Chem B., 2004, pp. 12429-12435, vol. 108.

Castro, S.L., et al., "Nanocrystalline Chalcopyrite Materials (CuInS(2)), and CuInSe(2)) via Low-Temperature Pyrolysis of Molecular Single-Source Precursors", Chem. Mater., 2003, pp. 3142-3147, vol. 15.

Choi, S.H., et al., "One-Pot Synthesis of Copper—Indium, Sulfide Nanocrystal Heterostructures with Acorn, Bottle, and Larva Shapes," J. Am Chem Soc., 2006, pp. 2520-2521, vol. 128 (8).

Connor et al., "Phase Transformation of Biphasic CuS#CuInS to Monophasic CuInS Nanorods," J. Am. Chem. Soc, 2009, 131 (13), 4962-4966.

De Faria, et al., "Sol-Gel TiO2 Thin Films Sensitized with the Mulberry Pigment Cyanidin," Materials Research, vol. 10, No. 4, 413-417, 2007.

Deivaraj et al., "Novel bimetallic thiocarboxylate compounds as single-source precursors to binary and ternary metal sulfide materials," Chem. Mater. (2003) 15:2383-2391.

Deivaraj et al., "Single-source precursors to ternary silver indium sulfide materials," Chem. Commun. (2001) 2304-2305.

Deniozou et al., "Surface structure of CuGASe2 (001)" Thin Solid Films 480-481 (2005) 382-387.

Domini, C.E, et al., "Comparison of three optimized digestion methods for rapid determination of chemical oxygen demand: Closed microwaves, open microwaves and ultrasound irradiation," Analytica Chimica Acta., 2006, pp. 210-217, vol. 561.

Dutta, D.P., et al., "A facile route to the synthesis of CuInS(2) nanoparticles," Materials Letters, 2006, pp. 2395-2398, vol. 60.

Gamallo-Lorenzo, D., et al., "Microwave-assisted alkaline digestion combined with microwave-assisted distillation for the determination of iodide and total iodine in edible seaweed by catalytic spectrophotometry," Analytica Chimica Acta., 2005, pp. 287-295, vol. 542.

(56) References Cited

OTHER PUBLICATIONS

Garcia-Vidal, J.A., et al., "Green chemistry: Efficient epoxides ring-opening with I-butanol under microwave irradiation," Applied Surface Science, 2006, pp. 6064-6066, vol. 252 (17).
Gardner et al., "Rapid synthesis and size control of CuInS2 semiconductor nanoparticles using microwave irradiation," J. Nanoparticle Research 2008, 10(4), pp. 633-641.
Gerbec, J.A., et al., "Microwave-Enhanced Reaction Rates for Nanoparticle Synthesis," J. Am. Chem. Soc., 2005, pp. 15791-15800, vol. 127.
Gratzel, M., "Perspectives for Dye-sensitized Nanocrystalline Solar Cells," Progress in Photovoltaics: Research and Applications, 2000, pp. 171-185, vol. 8.
Grisaru, H, et al., "Microwave-Assisted Polyol Synthesis of CuInTe(2) and CuInSe(2) Nanoparticles," Inorg. Chem., 2003, pp. 7148-7155, vol. 42.
Halgand et al., "Physico-chemical characterisation of Cu(In,Al)Se2 thin film for solar cells obtained by a selenisation process," Thin Solid Films 480-481 (2005) 443-446.
Hamid et al., "Preparation of Titanium Dioxide (TiO2) thin films by sol gel dip coating method," Malaysian Journal of Chemistry, 2003, vol. 5, No. 1, pp. 086-091.
Hayes, B.L., "Recent Advances in Microwave-Assisted Synthesis," Aldrichimica Acta., 2004, pp. 66-77, vol. 37 No. 2.
Hirashima et al., "Preparation of meso-porous TiO2 gels and their characterization," Journal of Non-Crystalline Solids 285 (2001) pp. 96-100.
Hirpo, Wakgari, et al., Synthesis of Mixed Copper—Indium Chalcogenolates. Single-Source Precursors for The Photovoltaic Materials CuInQ(2) (Q=S, Se), J. Am. Chem. Soc., 1993, pp. 1597-1599, vol. 115, No. 4.
Huynh, W.U., et al., "Hybrid Nanorod-Polymer Solar Cells," Science, 2002, pp. 2425-2427, vol. 295.
Huynh, W.U., et al., "CdSe Nanocrystal Rods/Poly (3-hexylthiophene) Composite Photovoltaic Devices," Advanced Materials, 1999, pp. 923-927, vol. 11 No. 11.
Jin et al., "Solar cells fabricated with CuInS2 films deposited using single-source precursors," Proceedings of the 19th European Photovoltaic Solar Energy Conference, 4AV.1.71, 2004.
Kim, K., et al., "Synthesis of CuInSe(2) and CuInGaSe(2) Nanoparticles by Solvothermal Route," Materials Science Forum, 2004, pp. 273-276, vols. 449-452.
Liu et al., "Preparation and characterization of CuInS2 thin films completely converted from CuInSe2 by sulfurization," Thin Solid Films 480-481 (2005) 50-54.
Luque, A., et al., "Increasing the Efficiency of Ideal Solar Cells by Photon Induced Transitions at Intermediate Levels," Physical Review Letters, 1997, pp. 5014-5017, vol. 78 No. 26.
Malik et al., "A novel route for the preparation of CuSe and CuInSe2 nanoparticles," Advanced Materials, (1999) 11:1441-1444.
Marcinkevicius, S., et al., "Changes in carrier dynamics induced by proton irradiation in quantum dots," Physica. B, Condensed Matter, 2002, pp. 203-206, vol. 314.
Miki et al., "Influence of calcination temperature on the microstructure of pourous TiO2 film," Materials Science Forum, vol. 569 (2008) pp. 17-20.
Murali, A., et al., Synthesis and Characterization of Indium Oxide Nanoparticles, Nano Letters, 2001, pp. 287-289, vol. 1, No. 6.
Nairn et al., "Preparation of Ultrafine Chalcopyrite Nanoparticles via the Photochemical Decomposition of Molecular Single-Source Precursors," Nano Letters 2006, vol. 6(6), pp. 1218-1223.
Norako et al., "Synthesis of Metastable Wurtzite CuInSe2Nanocrystals," Chem. Mater. 2010, 22, 1613-1615.
Navarro, P., et al., "Optimisation of microwave assisted digestion of sediments and determination of Sn and Hg," Analytica Chimica Acta, 2006, pp. 37-44, vol. 566.
Nüchter, M., et al., "Microwave Assisted Synthesis—a critical technology overview," Green Chem., 2004, pp. 128-141, vol. 6 (3).
Nüchter, M., et al., "Microwave-Assisted Chemical Reactions," Chem. Eng. Technol., 2003, 1207-1216, vol. 26 (12).
Paez et al., "Properties of Sol-Gel TiO2 Layers on Glass Substrate," Ceramics—Silikáty 48 (2) pp. 66-71 (2004).
Pak, J.J., et al., "An efficient synthesis of 4, 4' ,5,5'-tetraiododibenzo-24-crown-8 and its highly conjugated derivatives," Tetrahedron Letters, 2006, pp. 233-237, vol. 47.
Pan et al., "Synthesis of Cu—In—S Ternary Nanocrystals with Tunable Structure and Composition," J. Am. Chem. Soc. Apr. 30, 2008; 130(17):5620-1, Epub Apr. 9, 2008.
PCT International Search Report and Written Opinion of the International Searching Authority for PCT/US10/60583, dated Mar. 21, 2011, 12 pages.
Perozo-Rondon, E., et al., "Microwave enhanced synthesis of N-propargyl derivatives of imidazole A green approach for the preparation of fungicidal compounds," Applied Surface Science, 2006, pp. 6067-6070, vol. 252 (17).

METHODS OF FORMING SINGLE SOURCE PRECURSORS, METHODS OF FORMING POLYMERIC SINGLE SOURCE PRECURSORS, AND SINGLE SOURCE PRECURSORS FORMED BY SUCH METHODS

CROSS-REFERENCE TO RELATED APPLICATIONS

This application is a divisional of U.S. patent application Ser. No. 12/646,474, filed Dec. 23, 2009, now U.S. Pat. No.8,324,414, issued Dec. 4, 2012, the subject matter of which is related to the subject matter of U.S. patent application Ser. No. 13/191,062, filed Jul. 26, 2011, to the subject matter of U.S. patent application Ser. No. 13/099,043, filed May 2, 2011, now U.S. Pat. No. 8,445,388, issued May 21, 2013, which application is a divisional of U.S. patent application Ser. No. 12/047,956, filed Mar. 13, 2008, now U.S. Pat No. 8,003,070, issued Aug. 23, 2011, and to the subject matter of U.S. patent application Ser. No. 13/019,879, filed Feb. 2, 2011. The disclosure of each of the foregoing applications and patents is hereby incorporated herein in its entirety by this reference. The subject matter of this application is also related to the subject matter of U.S. patent application Ser. No. 13/365,800, filed Feb. 3, 2012.

GOVERNMENT RIGHTS

This invention was made under a Cooperative Research and Development Agreement between Precision Nanoparticles and Battelle Energy Alliance, LLC under Contract Number DE-AC07-051D14517 awarded by the United States Department of Energy. The government has certain rights in this invention.

TECHNICAL FIELD

Embodiments of the invention relate to methods of forming single source precursors and, more particularly, to methods of forming organometallic single source precursors for use in forming semiconductor materials, particles, and devices.

BACKGROUND

Semiconductor devices are devices that employ semiconductor materials, which are solid materials that exhibit an electrical conductivity lying between that of a conductor and that of an insulator. Semiconductor devices include, for example, diodes (e.g., light emitting diodes (LEDs)), photovoltaic devices, sensors, solid state lasers, and integrated circuits (e.g., memory modules and microprocessors).

Semiconductor materials that can be employed in semiconductor devices include, for example, silicon (Si), germanium (Ge), chalcopyrites (e.g., $CuInS_2$, $CuGaS_2$, and $CuInSe_2$), chalcogenides (e.g., $Cu(In_xGa_{1-x})(Se_yS_{1-y})_2$), cadmium telluride (CdTe), gallium arsenide (GaAs), organic polymers (e.g., polyphenylene vinylene, copper phthalocyanine, fullerenes), and light absorbing dyes (e.g., ruthenium-centered metalorganic dyes).

It has been discovered that chalcopyrite materials may be formed by decomposing one or more so-called "single source precursors" (SSPs), which are organometallic substances (e.g., molecules, complexes, etc.) that comprise all of the atomic elements, in the appropriate stoichiometric ratios, necessary to form a chalcopyrite material. Such methods, and methods of forming such SSPs are disclosed in, for example, Hirpo et al., *Synthesis of Mixed Copper-Indium Chalcogenolates. Single-Source Precursors for The Photovoltaic Materials* $CuInQ_2$ *(Q=S, Se)*, JOURNAL OF THE AMERICAN CHEMICAL SOCIETY, Vol. 115, Iss. 4, pp. 1597-1599 (Feb. 24, 1993). Methods for forming such SSPs are also disclosed in, for example, U.S. Pat. No. 6,992,202, which issued Jan. 31, 2006 to Banger et al.

There remains a need in the art, however, for improved methods that may be used to form single source precursors for use in forming chalcopyrite materials (e.g., semiconductive ternary chalcopyrite materials).

BRIEF SUMMARY

In some embodiments, the present invention includes methods of forming single source precursors. The methods include forming an intermediate product having the empirical formula $\frac{1}{2}\{L_2N(\mu-X)_2M'X_2\}_2$, and reacting MER with the intermediate product to form a single source precursor having the empirical formula $L_2N(\mu-ER)_2M'(ER)_2$, wherein L is a Lewis base coordinated to N by a dative bond, each M is individually selected from Group IA atoms, each N is individually selected from Group IB atoms, each M' is individually selected from Group IIIA atoms, each E is individually selected from Group VIA atoms, each X is individually selected from Group VIIA atoms or a nitrate group, and each R group is individually selected from the group consisting of alkyl, aryl, vinyl, (per)fluoro alkyl, (per)fluoro aryl, silane, and carbamato groups.

In some embodiments, the present invention includes methods of forming single source precursors from other single source precursors. For example, $HE^2R^2$ may be reacted with a first single source precursor having the empirical formula $L_2N(\mu-E^1R^1)_2M'(E^1R^1)_2$ to form a second, different single source precursor having the empirical formula $L_2N(\mu-E^2R^2)_2M'(E^2R^2)_2$, wherein L is a Lewis base coordinated to N by a dative bond, each N is individually selected from Group IB atoms, each M' is individually selected from Group IIIA atoms, each $E^1$ and $E^2$ is individually selected from Group VIA atoms, and each $R^1$ and $R^2$ group is individually selected from the group consisting of alkyl, aryl, vinyl, (per)fluoro alkyl, (per)fluoro aryl, silane, and carbamato groups.

In additional embodiments, the present invention includes methods of forming polymeric single source precursors, in which $HE^1R^1E^1H$ is reacted with a single source precursor having the empirical formula $L_2N(\mu-ER)_2M'(ER)_2$ to form a polymeric single source precursor having the empirical formula $[L_2N(\mu-ER)_a(\mu-E^1R^1E^1)_bM'(ER)_c(E^1R^1E^1)_d]_m$, wherein L is a Lewis base coordinated to N by a dative bond, each N is individually selected from Group IB atoms, each M' is individually selected from Group IIIA atoms, each E and $E^1$ is individually selected from Group VIA atoms, a is any number from zero (0) to two (2), b is the difference between two (2) and a (b=2−a), c is any number from zero (0) to two (2), d is the difference between two (2) and c (d=2−c), m is any number, each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of aryl, vinyl, (per)fluoro alkyl, (per)fluoro aryl, silane, carbamato, and α,ω-$E^1$ functionalized alkyl groups.

In additional embodiments, the present invention includes methods of forming polymeric single source precursors in which at least one of $HE^1R^1E^1H$ and $HE^2R^2$ is reacted with a single source precursor having the empirical formula $L_2N(\mu-ER)_2M'(ER)_2$ to form a polymeric single source precursor having the empirical formula $[L_2N(E^2R^2)_a(\mu-E^1R^1E^1)_bM'$ $(E^2R^2)_c(E^1R^1E^1)_d]_m$, wherein L is a Lewis base coordinated to N by a dative bond, each N is individually selected from Group IB atoms, each M' is individually selected from Group IIIA atoms, each E, $E^1$, and $E^2$ is individually selected from Group VIA atoms, a is any number from zero (0) to two (2), b is the difference between two (2) and a, c is any number from zero (0) to two (2), d is the difference between two (2) and c, m is any number, each R and $R^2$ is individually selected from the group consisting of alkyl, aryl, vinyl, (per)fluoro alkyl, (per)fluoro aryl, silane, and carbamato groups, and each $R^1$ is individually selected from the group consisting of aryl, vinyl, (per)fluoro alkyl, (per)fluoro aryl, silane, carbamato, and α,ω-$E^1$ functionalized alkyl groups.

In yet further embodiments, the present invention includes methods of forming copolymeric single source precursors in which a first single source precursor, a second single source precursor differing from the first single source precursor, and $HE^1R^1E^1H$ are reacted to form a copolymeric single source precursor having the empirical formula $\{[L_2N^1(ER)_a(\mu\text{-}E^1R^1E^1)_bM^{r1}(ER)_c(E^1R^1E^1)_d]_m[L_2N^2(ER)_e(\mu\text{-}E^1R^1E^1)_fM^{r2}(ER)_g(E^1R^1E^1)_h]_n\}_l$, wherein L is a Lewis base, each $N^1$ and $N^2$ is individually selected from Group IB atoms, each $M^{r1}$ and $M^{r2}$ is individually selected from Group IIIA atoms, each E and $E^1$ is individually selected from Group VIA atoms, a is any number from zero (0) to two (2), b is the difference between two (2) and a, c is any number from zero (0) to two (2), d is the difference between two (2) and c, e is any number from zero (0) to two (2), f is the difference between two (2) and e, g is any number from zero (0) to two (2), h is the difference between two (2) and g, m is any number, n is any number, l is any number, each R is individually selected from the group consisting of alkyl, aryl, vinyl, (per)fluoro alkyl, (per)fluoro aryl, silane, and carbamato groups, and each $R^1$ is individually selected from the group consisting of aryl, vinyl, (per)fluoro alkyl, (per)fluoro aryl, silane, carbamato, and α,ω-$E^1$ functionalized alkyl groups.

Additional embodiments of the present invention include methods of forming polymeric single source precursors in which at least one of $ME^1R^1E^1M$ and MER is reacted with a substance having the empirical formula $L_2N(\mu\text{-}X)_2M'(X)_2$ to form a polymeric single source precursor having the empirical formula $[L_2N(\mu\text{-}ER)_a(\mu\text{-}E^1R^1E^1)_bM'(ER)_c(E^1R^1E^1)_d]_m$, wherein L is a Lewis base that is coordinated to N by a dative bond, each M is individually selected from Group IA atoms, each N is individually selected from Group IB atoms, each M' is individually selected from Group IIIA atoms, each E and $E^1$ is individually selected from Group VIA atoms, each X is individually selected from Group VIIA atoms or a nitrate group, a is any number from zero (0) to two (2), b is the difference between two (2) and a (b=2−a), c is any number from zero (0) to two (2), d is the difference between two (2) and c (d=2−c), m is any number, each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of aryl, vinyl, (per)fluoro alkyl, (per)fluoro aryl, silane, carbamato, and α,ω-$E^1$ functionalized alkyl groups.

In additional embodiments, copolymeric single source precursors are formed by reacting $uME^1R^1E^1M$ and vMER with a first substance having the empirical formula $L_2N^1(\mu\text{-}X)_2M^{r1}(X)_2$ and a second substance having the empirical formula $L_2N^2(\mu\text{-}X)_2M^{r2}(X)_2$ to form a copolymeric single source precursor having the empirical formula $\{[L_2N^1(ER)_a(\mu\text{-}E^1R^1E^1)_bM^{r1}(ER)_c(E^1R^1E^1)_d]_m[L_2N^2(ER)_e(\mu\text{-}E^1R^1E^1)_fM^{r2}(ER)_g(E^1R^1E^1)_h]_n\}_l$, wherein L is a Lewis base, each $N^1$ and $N^2$ is individually selected from Group IB atoms, each $M^{r1}$ and $M^{r2}$ is individually selected from Group IIIA atoms, each E and $E^1$ is individually selected from Group VIA atoms, a is any number from zero (0) to two (2), b is the difference between two (2) and a, c is any number from zero (0) to two (2), d is the difference between two (2) and c, e is any number from zero (0) to two (2), f is the difference between two (2) and e, g is any number from zero (0) to two (2), h is the difference between two (2) and g, m is any number, n is any number, l is any number, u is any number from zero (0) to four (4), v is the difference between four (4) and u, each R is individually selected from the group consisting of alkyl, aryl, vinyl, (per)fluoro alkyl, (per)fluoro aryl, silane, and carbamato groups, and each $R^1$ is individually selected from the group consisting of aryl, vinyl, (per)fluoro alkyl, (per)fluoro aryl, silane, carbamato, and α,ω-$E^1$ functionalized alkyl groups.

Further embodiments of the present invention include single source precursors, polymeric single source precursors, and copolymeric single source precursors formed by the methods described herein.

For example, in some embodiments, the present invention includes polymeric, organometallic single source precursor having the empirical formula $[L_2N(ER)_a(\mu\text{-}E^1R^1E^1)_bM'(ER)_c(E^1R^1E^1)_d]_m$, wherein L is a Lewis base, each N is individually selected from Group IB atoms, each M' is individually selected from Group IIIA atoms, each E and $E^1$ is individually selected from Group VIA atoms, a is any number from zero (0) to two (2), b is the difference between two (2) and a, c is any number from zero (0) to two (2), d is the difference between two (2) and c, m is any number, each R is individually selected from the group consisting of alkyl, aryl, vinyl, (per)fluoro alkyl, (per)fluoro aryl, silane, and carbamato groups, and each $R^1$ is individually selected from the group consisting of aryl, vinyl, (per)fluoro alkyl, (per)fluoro aryl, silane, carbamato, and α,ω-$E^1$ functionalized alkyl groups.

Yet further embodiments of the present invention include polymeric, organometallic single source precursors having the empirical formula $[L_2N(\mu ER^1)_a(\mu\text{-}ER^2E)_bM'(ER^1)_c(ER^2E)_d]_m$, wherein L is a Lewis base, each N is individually selected from Group IB atoms, each M' is individually selected from Group IIIA atoms, each E is individually selected from Group VIA atoms, a is any number from zero (0) to two (2), b is the difference between two (2) and a (b=2−a), c is any number from zero (0) to two (2), d is the difference between two (2) and c (d=2−c), m is any number, each of the $R^1$ groups is individually selected from the group consisting of alkyl, aryl, vinyl, (per)fluoro alkyl, (per)fluoro aryl, silane, and carbamato groups, and each of the $R^2$ groups is individually selected from the group consisting of alkyl, vinyl, and aryl groups.

BRIEF DESCRIPTION OF THE SEVERAL VIEWS OF THE DRAWINGS

While the specification concludes with claims particularly pointing out and distinctly claiming that which is regarded as the present invention, advantages of this invention may be more readily ascertained from the following description of the invention when read in conjunction with the accompanying drawings in which:

DETAILED DESCRIPTION

Figure 1:
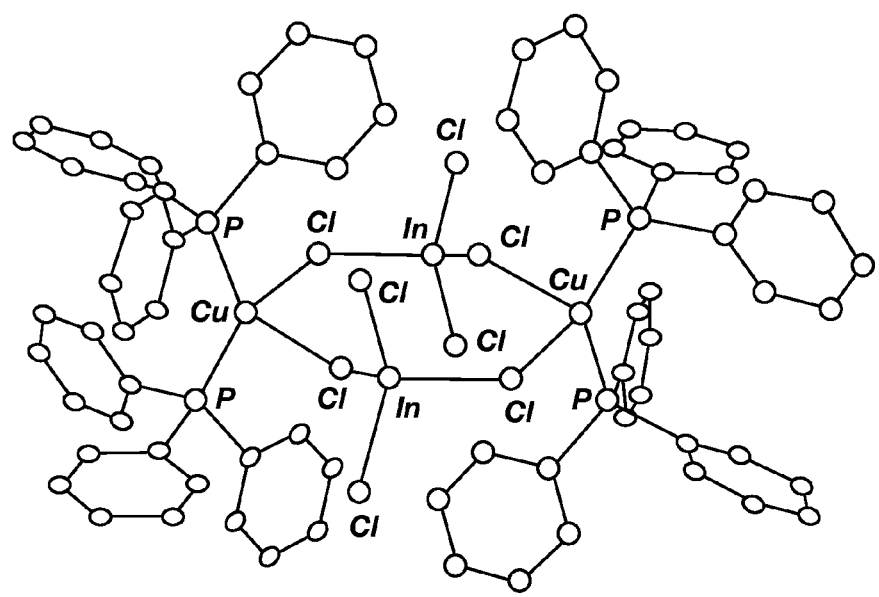
FIGS. 1 through 4 illustrate various intermediate products that may be formed in accordance with embodiments of methods of the present invention for forming single source precursors.

The illustrations presented herein are not meant to be actual views of any particular molecule or complex, but are merely idealized representations that are employed to describe various embodiments of the present invention.

The chalcogens are the elements in Group VIA (16) of the periodic table. As used herein, the term "chalcogenide" means and includes any compound that contains at least one chalcogen element other than oxygen (e.g., sulfur, selenium, tellurium, etc.). Chalcogenides include, for example, ternary chalcopyrite materials.

As used herein the term "ternary chalcopyrite material" means and includes any material having a composition generally represented by the formula I-III-VI$_2$, where roman numeral I refers to elements in Group I (Groups IA (1) and IB (11)) of the periodic table, roman numeral III refers to elements in Group III (Groups IIIB (3) and IIIA (13)) of the periodic table, and roman numeral VI refers to elements in Group VI (Groups VIB (6) and VIA (16)) of the periodic table. By ternary, it is meant that the chalcopyrite materials contain atoms from three elemental Groups of the periodic table. For example, approximately twenty-five percent (25%) of the atoms in a ternary chalcopyrite material may be from Group IB, approximately twenty-five percent (25%) of the atoms may be from Group IIIA, and approximately fifty percent (50%) of the atoms may be from Group VIA. CuInS$_2$, CuInSe$_2$, Cu(In,Ga)Se$_2$, CuGaSe$_2$, and AgInS$_2$ are examples of ternary chalcopyrite materials. It should be noted that ternary chalcopyrites include materials having multiple and/or different atoms from each of three Groups of the periodic table. For example, CuInSSe is a ternary chalcopyrite because it has Cu (Group IB), In (Group IIIA), and S and Se (both from Group VIA). In addition, materials of the form (Cu:Ag)(In:Ga)(S:Se), having various ratios of the respectively grouped atoms are all ternary chalcopyrites (Cu and Ag both are in Group IB, In and Ga both are in Group IIIA, S and Se both are in Group VIA).

As used herein, the terms "single source precursor" and "SSP" mean and include any substance (e.g., a molecule or complex) that comprises all of the necessary atomic elements, in the appropriate stoichiometric ratios, necessary to form a chalcogenide material (e.g., a ternary chalcopyrite material). Single source precursors may comprise so-called organometallic substances. As non-limiting examples, single source precursors include molecules or complexes having the empirical formula [L$_2$N(μ-ER)$_2$M(ER)$_2$] (or L$_2$NM(ER)$_4$), wherein L is a Lewis base that is coordinated to N by a dative bond, each N is individually selected from Group IB atoms, each M is individually selected from Group IIIA atoms, each E is individually selected from Group VIA atoms, and each R is individually selected from the group consisting of alkyl, aryl, vinyl, (per)fluoro alkyl, (per)fluoro aryl, silane, and carbamato groups. As seven particular non-limiting examples, single source precursors include (Ph$_3$P)$_2$Cu(μ-SEt)$_2$In(SEt)$_2$, (Ph$_3$P)$_2$Cu(μ-SEt)$_2$Ga(SEt)$_2$, (Ph$_3$P)$_2$Cu(μ-SEt)$_2$Al(SEt)$_2$, (Ph$_3$P)$_2$Ag(μ-SEt)$_2$In(SEt)$_2$, (Ph$_3$P)$_2$Ag(μ-SEt)$_2$Ga(SEt)$_2$, (Ph$_3$P)$_2$Ag(μ-SEt)$_2$Al(SEt)$_2$, and {(Ph$_3$P)$_2$Cu(μ-Cl)$_2$InCl$_2$}$_2$.

By way of example and not limitation, the following are examples of copper-indium SSPs: [bis(ethanethiolato)indium]bis[μ-(ethanethiolato)]bis(triisobutylphosphine)-copper; [bis(ethanethiolato)indium]bis[μ-(ethanethiolato)]bis(trihexylphosphine)-copper; [bis(ethanethiolato)indium]bis[μ-(ethanethiolato)]bis(triphenylphosphine)-copper; [bis(ethanethiolato)indium]bis[μ-(ethanethiolato)]bis(perfluorotriphenylphosphine)-copper; [bis(propanethiolato)indium]bis[μ-(propanethiolato)]bis(triisobutylphosphine)-copper; [bis(propanethiolato)indium]bis[μ-(propanethiolato)]bis(trihexylphosphine)-copper; [bis(propanethiolato)indium]bis[μ-(propanethiolato)]bis(triphenylphosphine)-copper; [bis(propanethiolato)indium]bis[μ-(propanethiolato)]bis(perfluorotriphenylphosphine)-copper; [bis(hexanethiolato)indium]bis[μ-(propanethiolato)]bis(triisobutylphosphine)-copper; [bis(hexanethiolato)indium]bis[μ-(propanethiolato)]bis(trihexylphosphine)-copper; [bis(hexanethiolato)indium]bis[μ-(propanethiolato)]bis(triphenylphosphine)-copper; [bis(hexanethiolato)indium]bis[μ-(propanethiolato)]bis(perfluorotriphenylphosphine)-copper; [bis(4-trifluoromethyl-thiophenolato)indium]bis[μ-(4-trifluoromethylthiophenolato)]bis(triisobutylphosphine)-copper; [bis(4-trifluoromethyl-thiophenolato)indium]bis[μ-(4-trifluoromethyl-thiophenolato)]bis(trihexylphosphine)-copper; [bis(4-trifluoromethyl-thiophenolato)indium]bis[μ-(4-trifluoromethyl-thiophenolato)]bis(triphenylphosphine)-copper; [bis(4-trifluoromethyl-thiophenolato)indium]bis[μ-(4-trifluoromethyl-thiophenolato)]bis(perfluorotriphenylphosphine)-copper; [bis(3,5-bis(trifluoromethyl)-thiophenolato)indium]bis[μ-(3,5-bis(trifluoromethyl)-thiophenolato)]bis(triisobutylphosphine)-copper; [bis(3,5-bis(trifluoromethyl)-thiophenolato)indium]bis[μ-(3,5-bis(trifluoromethyl)-thiophenolato)]bis(trihexylphosphine)-copper; [bis(3,5-bis(trifluoromethyl)-thiophenolato) indium]bis[μ-(3,5-bis(trifluoromethyl)-thiophenolato)]bis(triphenylphosphine)-copper; [bis(3,5-bis(trifluoromethyl)-thiophenolato)indium]bis[μ-(3,5-bis(trifluoromethyl)-thiophenolato)]bis(perfluorotriphenylphosphine)-copper; [bis(thiophenolato)indium]bis[μ-(thiophenolato)]bis(triisobutylphosphine)-copper; [bis(thiophenolato)indium]bis[μ-(thiophenolato)]bis(trihexylphosphine)-copper; [bis(thiophenolato)indium]bis[μ-(thiophenolato)]bis(triphenylphosphine)-copper; [bis(thiophenolato)indium]bis[μ-(thiophenolato)]bis(perfluorotriphenylphosphine)-copper; [bis(α-toluenethiolato)indium]bis[μ-(α-toluenethiolato)]bis(triisobutylphosphine)-copper; [bis(α-toluenethiolato)indium]bis[μ-(α-toluenethiolato)]bis(trihexylphosphine)-copper; [bis(α-toluenethiolato)indium]bis[μ-(α-toluenethiolato)]bis(triphenylphosphine)-copper; [bis(α-toluenethiolato)indium]bis [μ-(α-toluenethiolato)]bis(perfluorotriphenylphosphine)-copper; [bis(pentafluorothiophenolato) indium]bis[μ-(pentafluorothiophenolato)]bis(triisobutylphosphine)-copper; [bis(pentafluorothiophenolato)indium]bis[μ-(pentafluorothiophenolato)]bis(trihexylphosphine)-copper; [bis(pentafluorothiophenolato)indium]bis[μ-(pentafluorothiophenolato)]bis(triphenylphosphine)-copper; [bis(pentafluorothiophenolato)indium]bis [μ-(pentafluorothiophenolato)]bis(perfluorotriphenylphosphine)-copper; [bis(thiobenzoato)indium]bis[μ-(thiobenzoato)]bis(triisobutylphosphine)-copper; [bis(thiobenzoato)indium]bis[μ-(thiobenzoato)]bis(trihexylphosphine)-copper; [bis(thiobenzoato)indium]bis[μ-(thiobenzoato)]bis(triphenylphosphine)-copper; [bis(thiobenzoato)indium]bis[μ-(thiobenzoato)]bis(perfluorotriphenylphosphine)-copper; [bis(thiobenzoato)indium]bis[μ-(thiobenzoato)]bis[ethylenebis(diphenylphosphine)]-copper; [bis(thiobenzoato)indium]bis[μ-(thiobenzoato)]bis[bis(2-diphenylphosphinophenyl)ether]-copper; [bis(thiobenzoato)indium]bis[μ-(thiobenzoato)]bis(trimethylphosphine)-copper; [bis(ethanethiolato)indium]bis[μ-(ethanethiolato)]bis

[ethylenebis(diphenylphosphine)]-copper; [bis(ethanethiolato)indium]bis[μ-(ethanethiolato)]bis[bis(2-diphenylphosphinophenyl)ether]-copper; [bis(ethanethiolato)indium]bis[μ-(thiophenolato)]bis(triphenylphosphine)-copper; and [bis(ethanethiolato)indium]bis[μ-(ethanethiolato)]bis(trimethylphosphine)-copper.

By way of example and not limitation, the following are examples of copper-gallium SSPs: [bis(ethanethiolato)gallium]bis[μ-(ethanethiolato)]bis(triisobutylphosphine)-copper; [bis(ethanethiolato)gallium]bis[μ-(ethanethiolato)]bis(trihexylphosphine)-copper; [bis(ethanethiolato)gallium]bis[μ-(ethanethiolato)]bis(triphenylphosphine)-copper; [bis(ethanethiolato)gallium]bis[μ-(ethanethiolato)]bis(perfluorotriphenylphosphine)-copper; [bis(propanethiolato)gallium]bis[μ-(propanethiolato)]bis(triisobutylphosphine)-copper; [bis(propanethiolato)gallium]bis[μ-(propanethiolato)]bis(trihexylphosphine)-copper; [bis(propanethiolato)gallium]bis[μ-(propanethiolato)]bis(triphenylphosphine)-copper; [bis(propanethiolato)gallium]bis[μ-(propanethiolato)]bis(perfluorotriphenylphosphine)-copper; [bis(hexanethiolato)gallium]bis[μ-(propanethiolato)]bis(triisobutylphosphine)-copper; [bis(hexanethiolato)gallium]bis[μ-(propanethiolato)]bis(trihexylphosphine)-copper; [bis(hexanethiolato)gallium]bis[μ-(propanethiolato)]bis(triphenylphosphine)-copper; [bis(hexanethiolato)gallium]bis[μ-(propanethiolato)]bis(perfluorotriphenylphosphine)-copper; [bis(4-trifluoromethyl-thiophenolato)gallium]bis[μ-(4-trifluoromethyl-thiophenolato)]bis(triisobutylphosphine)-copper; [bis(4-trifluoromethyl-thiophenolato)gallium]bis[μ-(4-trifluoromethyl-thiophenolato)]bis(trihexylphosphine)-copper; [bis(4-trifluoromethyl-thiophenolato)gallium]bis[μ-(4-trifluoromethyl-thiophenolato)]bis(triphenylphosphine)-copper; [bis(4-trifluoromethyl-thiophenolato)gallium]bis[μ-(4-trifluoromethyl-thiophenolato)]bis(perfluorotriphenylphosphine)-copper; [bis(3,5-bis(trifluoromethyl)-thiophenolato)gallium]bis[μ-(3,5-bis(trifluoromethyl)thiophenolato)]bis(triisobutylphosphine)-copper; [bis(3,5-bis(trifluoromethyl)-thiophenolato)gallium]bis[μ-(3,5-bis(trifluoromethyl)-thiophenolato)]bis(trihexylphosphine)-copper; [bis(3,5-bis(trifluoromethyl)-thiophenolato) gallium]bis[μ-(3,5-bis(trifluoromethyl)-thiophenolato)]bis(triphenylphosphine)-copper; [bis(3,5-bis(trifluoromethyl)-thiophenolato) gallium]bis[μ-(3,5-bis(trifluoromethyl)-thiophenolato)]bis(perfluorotriphenylphosphine)-copper; [bis(thiophenolato)gallium]bis[μ-(thiophenolato)]bis(triisobutylphosphine)-copper; [bis(thiophenolato)gallium]bis[μ-(thiophenolato)]bis(trihexylphosphine)-copper; [bis(thiophenolato)gallium]bis[μ-(thiophenolato)]bis(triphenylphosphine)-copper; [bis(thiophenolato)gallium]bis[μ-(thiophenolato)]bis(perfluorotriphenylphosphine)-copper; [bis(α-toluenethiolato)gallium]bis[μ-(α-toluenethiolato)]bis(triisobutylphosphine)-copper; [bis(α-toluenethiolato)gallium]bis[μ-(α-toluenethiolato)]bis(trihexylphosphine)-copper; [bis(α-toluenethiolato)gallium]bis[μ-(α-toluenethiolato)]bis(triphenylphosphine)-copper; [bis(α-toluenethiolato)gallium]bis[μ-(α-toluenethiolato)]bis(perfluorotriphenylphosphine)-copper; [bis(pentafluorothiophenolato)gallium]bis[μ-(pentafluorothiophenolato)]bis(triisobutylphosphine)-copper; [bis(pentafluorothiophenolato)gallium]bis[μ-(pentafluorothiophenolato)]bis(trihexylphosphine)-copper; [bis(pentafluorothiophenolato)gallium]bis[μ-(pentafluorothiophenolato)]bis(triphenylphosphine)-copper; and [bis(pentafluorothiophenolato)gallium]bis[μ-(pentafluorothiophenolato)]bis(perfluorotriphenylphosphine)-copper.

By way of example and not limitation, the following are examples of silver-indium SSPs: [bis(ethanethiolato)indium]bis[μ-(ethanethiolato)]bis(triisobutylphosphine)-silver; [bis(ethanethiolato)indium]bis[μ-(ethanethiolato)]bis(trihexylphosphine)-silver; [bis(ethanethiolato)indium]bis[μ-(ethanethiolato)]bis(triphenylphosphine)-silver; [bis(ethanethiolato)indium]bis[μ-(ethanethiolato)]bis(perfluorotriphenylphosphine)-silver; [bis(propanethiolato)indium]bis[μ-(propanethiolato)]bis(triisobutylphosphine)-silver; [bis(propanethiolato)indium]bis[μ-(propanethiolato)]bis(trihexylphosphine)-silver; [bis(propanethiolato)indium]bis[μ-(propanethiolato)]bis(triphenylphosphine)-silver; [bis(propanethiolato)indium]bis[μ-(propanethiolato)]bis(perfluorotriphenylphosphine)-silver; [bis(hexanethiolato)indium]bis[μ-(propanethiolato)]bis(triisobutylphosphine)-silver; [bis(hexanethiolato)indium]bis[μ-(propanethiolato)]bis(trihexylphosphine)-silver; [bis(hexanethiolato)indium]bis[μ-(propanethiolato)]bis(triphenylphosphine)-silver; [bis(hexanethiolato)indium]bis[μ-(propanethiolato)]bis(perfluorotriphenylphosphine)-silver; [bis(4-trifluoromethyl-thiophenolato)indium]bis[μ-(4-trifluoromethyl-thiophenolato)]bis(triisobutylphosphine)-silver; [bis(4-trifluoromethyl-thiophenolato)indium]bis[μ-(4-trifluoromethyl-thiophenolato)]bis(trihexylphosphine)-silver; [bis(4-trifluoromethyl-thiophenolato)indium]bis[μ-(4-trifluoromethyl-thiophenolato)]bis(triphenylphosphine)-silver; [bis(4-trifluoromethyl-thiophenolato)indium]bis[μ-(4-trifluoromethyl-thiophenolato)]bis(perfluorotriphenylphosphine)-silver; [bis(3,5-bis(trifluoromethyl)-thiophenolato)indium]bis[μ-(3,5-bis(trifluoromethyl)-thiophenolato)]bis(triisobutylphosphine)-silver; [bis(3,5-bis(trifluoromethyl)-thiophenolato)indium]bis[μ-(3,5-bis(trifluoromethyl)-thiophenolato)]bis(trihexylphosphine)-silver; [bis(3,5-bis(trifluoromethyl)-thiophenolato) indium]bis[μ-(3,5-bis(trifluoromethyl)-thiophenolato)]bis(triphenylphosphine)-silver; and [bis(3,5-bis(trifluoromethyl)-thiophenolato)indium]bis[μ-(3,5-bis(trifluoromethyl)-thiophenolato)]bis(perfluorotriphenylphosphine)-silver.

By way of example and not limitation, the following are examples of silver-gallium SSPs: [bis(ethanethiolato)gallium]bis[μ-(ethanethiolato)]bis(triisobutylphosphine)-silver; [bis(ethanethiolato)gallium]bis[μ-(ethanethiolato)]bis(trihexylphosphine)-silver; [bis(ethanethiolato)gallium]bis[μ-(ethanethiolato)]bis(triphenylphosphine)-silver; [bis(ethanethiolato)gallium]bis[μ-(ethanethiolato)]bis(perfluorotriphenylphosphine)-silver; [bis(propanethiolato)gallium]bis[μ-(propanethiolato)]bis(triisobutylphosphine)-silver; [bis(propanethiolato)gallium]bis[μ-(propanethiolato)]bis(trihexylphosphine)-silver; [bis(propanethiolato)gallium]bis[μ-(propanethiolato)]bis(triphenylphosphine)-silver; [bis(propanethiolato)gallium]bis[μ-(propanethiolato)]bis(perfluorotriphenylphosphine)-silver; [bis(hexanethiolato)gallium]bis[μ-(propanethiolato)]bis(triisobutylphosphine)-silver; [bis(hexanethiolato)gallium]bis[μ-(propanethiolato)]bis(trihexylphosphine)-silver; [bis(hexanethiolato)gallium]bis[μ-(propanethiolato)]bis(triphenylphosphine)-silver; [bis(hexanethiolato)gallium]bis[μ-(propanethiolato)]bis(perfluorotriphenylphosphine)-silver; [bis(4-trifluoromethyl-thiophenolato)gallium]bis[μ-(4-trifluoromethyl-thiophenolato)]bis(triisobutylphosphine)-silver; [bis(4-trifluoromethyl-thiophenolato)gallium]bis[μ-(4-trifluoromethyl-thiophenolato)]bis(trihexylphosphine)-silver; [bis(4-trifluoromethyl-thiophenolato)gallium]bis[μ-(4- trifluoromethyl-thiophenolato)]bis(triphenylphosphine)-silver; [bis(4-trifluoromethyl-thiophenolato)gallium]bis[μ-(4-trifluoromethyl-thiophenolato)]bis(perfluorotriphenylphosphine)-silver; [bis(3,5-bis(trifluoromethyl)-thiophenolato)gallium]bis[μ-(3,5-bis(trifluoromethyl)-thiophenolato)]bis(triisobutylphosphine)-silver; [bis(3,5-bis(trifluoromethyl)-thiophenolato)gallium]bis[μ-(3,5-bis(trifluoromethyl)-thiophenolato)]bis(trihexylphosphine)-silver; [bis(3,5-bis(trifluoromethyl)-thiophenolato) gallium]bis[μ-(3,5-bis(trifluoromethyl)-thiophenolato)]bis(triphenylphosphine)-silver; [bis(3,5-bis(trifluoromethyl)-thiophenolato)gallium]bis[μ-(3,5-bis(trifluoromethyl)-thiophenolato)]bis(perfluorotriphenylphosphine)-silver; [bis(thiophenolato)gallium]bis [μ-(thiophenolato)]bis(triisobutylphosphine)-silver; [bis(thiophenolato)gallium]bis [μ-(thiophenolato)]bis(trihexylphosphine)-silver; [bis(thiophenolato)gallium]bis[μ-(thiophenolato)]bis(triphenylphosphine)-silver; [bis(thiophenolato)gallium]bis[μ-(thiophenolato)]bis(perfluorotriphenylphosphine)-silver; [bis(α-toluenethiolato)gallium]bis[μ-(α-toluenethiolato)]bis(triisobutylphosphine)-silver; [bis(α-toluenethiolato)gallium]bis [μ-(α-toluenethiolato)]bis(trihexylphosphine)-silver; [bis(α-toluenethiolato)gallium]bis [μ-(α-toluenethiolato)]bis(triphenylphosphine)-silver; [bis(α-toluenethiolato)gallium]bis [μ-(α-toluenethiolato)]bis(perfluorotriphenylphosphine)-silver; [bis(pentafluorothiophenolato) gallium]bis[μ-(pentafluorothiophenolato)]bis(triisobutylphosphine)-silver; [bis(pentafluorothiophenolato)gallium]bis[μ-(pentafluorothiophenolato)]bis(trihexylphosphine)-silver; [bis(pentafluorothiophenolato)gallium]bis[μ-(pentafluorothiophenolato)]bis(triphenylphosphine)-silver; and [bis(pentafluorothiophenolato)gallium]bis [μ-(pentafluorothiophenolato)]bis(perfluorotriphenylphosphine)-silver.

By way of example and not limitation, the following are examples of copper-aluminum SSPs: [bis(ethanethiolato)aluminum]bis[μ-(ethanethiolato)]bis(triisobutylphosphine)-copper; [bis(ethanethiolato)aluminum]bis[μ-(ethanethiolato)]bis(trihexylphosphine)-copper; [bis(ethanethiolato)aluminum]bis[μ-(ethanethiolato)]bis (triphenylphosphine)-copper; [bis(ethanethiolato)aluminum]bis[μ-(ethanethiolato)]bis(perfluorotriphenylphosphine)-copper; [bis(propanethiolato)aluminum]bis[μ-(propanethiolato)]bis(triisobutylphosphine)-copper; [bis(propanethiolato)aluminum]bis[μ-(propanethiolato)]bis(trihexylphosphine)-copper; [bis(propanethiolato)aluminum]bis[μ-(propanethiolato)]bis(triphenylphosphine)-copper; [bis(propanethiolato)aluminum]bis[μ-(propanethiolato)]bis(perfluorotriphenylphosphine)-copper; [bis(hexanethiolato)aluminum]bis[μ-(propanethiolato)]bis(triisobutylphosphine)-copper; [bis(hexanethiolato)aluminum]bis[μ-(propanethiolato)]bis(trihexylphosphine)-copper; [bis(hexanethiolato)aluminum]bis[μ-(propanethiolato)]bis(triphenylphosphine)-copper; [bis(hexanethiolato)aluminum]bis[μ-(propanethiolato)]bis(perfluorotriphenylphosphine)-copper; [bis(4-trifluoromethyl-thiophenolato)aluminum]bis[μ-(4-trifluoromethylthiophenolato)]bis(triisobutylphosphine)-copper; [bis(4-trifluoromethyl-thiophenolato)aluminum]bis[μ-(4-trifluoromethyl-thiophenolato)]bis(trihexylphosphine)-copper; [bis(4-trifluoromethyl-thiophenolato)aluminum]bis[μ-(4-trifluoromethyl-thiophenolato)]bis(triphenylphosphine)-copper; [bis(4-trifluoromethyl-thiophenolato)aluminum]bis[μ-(4-trifluoromethyl-thiophenolato)]bis(perfluorotriphenylphosphine)-copper; [bis(3,5-bis(trifluoromethyl)-thiophenolato)aluminum]bis[μ-(3,5-bis(trifluoromethyl)-thiophenolato)]bis(triisobutylphosphine)-copper; [bis(3,5-bis(trifluoromethyl)-thiophenolato)aluminum]bis[μ-(3,5-bis(trifluoromethyl)-thiophenolato)]bis(trihexylphosphine)-copper; [bis(3,5-bis(trifluoromethyl)-thiophenolato)aluminum]bis[μ-(3,5-bis(trifluoromethyl)-thiophenolato)]bis(triphenylphosphine)-copper; [bis(3,5-bis(trifluoromethyl)-thiophenolato) aluminum]bis[μ-(3,5-bis(trifluoromethyl)-thiophenolato)]bis(perfluorotriphenylphosphine)-copper; [bis(thiophenolato)aluminum]bis[μ-(thiophenolato)]bis(triisobutylphosphine)-copper; [bis(thiophenolato)aluminum]bis[μ-(thiophenolato)]bis(trihexylphosphine)-copper; [bis(thiophenolato)aluminum]bis[μ-(thiophenolato)]bis(triphenylphosphine)-copper; [bis(thiophenolato)aluminum]bis[μ-(thiophenolato)]bis(perfluorotriphenylphosphine)-copper; [bis(α-toluenethiolato)aluminum]bis[μ-(α-toluenethiolato)]bis(triisobutylphosphine)-copper; [bis(α-toluenethiolato)aluminum]bis[μ-(α-toluenethiolato)]bis(trihexylphosphine)-copper; [bis(α-toluenethiolato)aluminum]bis[μ-(α-toluenethiolato)]bis(triphenylphosphine)-copper; [bis(α-toluenethiolato)aluminum]bis[μ-(α-toluenethiolato)]bis(perfluorotriphenylphosphine)-copper; [bis(pentafluorothiophenolato)aluminum]bis[μ-(pentafluorothiophenolato)]bis(triisobutylphosphine)-copper; [bis(pentafluorothiophenolato)aluminum]bis[μ-(pentafluorothiophenolato)]bis(trihexylphosphine)-copper; [bis(pentafluorothiophenolato)aluminum]bis[μ-(pentafluorothiophenolato)]bis(triphenylphosphine)-copper; and [bis(pentafluorothiophenolato)aluminum]bis[μ-(pentafluorothiophenolato)]bis(perfluorotriphenylphosphine)-copper.

By way of example and not limitation, the following are examples of silver-aluminum SSPs: [bis(ethanethiolato)aluminum]bis[μ-(ethanethiolato)]bis(triisobutylphosphine)-silver; [bis(ethanethiolato)aluminum]bis[μ-(ethanethiolato)]bis(trihexylphosphine)-silver; [bis(ethanethiolato)aluminum]bis[μ-(ethanethiolato)]bis(triphenylphosphine)-silver; [bis(ethanethiolato)aluminum]bis[μ-(ethanethiolato)]bis(perfluorotriphenylphosphine)-silver; [bis(propanethiolato)aluminum]bis[μ-(propanethiolato)]bis(triisobutylphosphine)-silver; [bis(propanethiolato)aluminum]bis[μ-(propanethiolato)]bis(trihexylphosphine)-silver; [bis(propanethiolato)aluminum]bis[μ-(propanethiolato)]bis(triphenylphosphine)-silver; [bis(propanethiolato)aluminum]bis[μ-(propanethiolato)]bis(perfluorotriphenylphosphine)-silver; [bis(hexanethiolato)aluminum]bis[μ-(propanethiolato)]bis(triisobutylphosphine)-silver; [bis(hexanethiolato)aluminum]bis[μ-(propanethiolato)]bis(trihexylphosphine)-silver; [bis(hexanethiolato)aluminum]bis[μ-(propanethiolato)]bis(triphenylphosphine)-silver; [bis(hexanethiolato)aluminum]bis[μ-(propanethiolato)]bis(perfluorotriphenylphosphine)-silver; [bis(4-trifluoromethyl-thiophenolato)aluminum]bis[μ-(4-trifluoromethylthiophenolato)]bis(triisobutylphosphine)-silver; [bis(4-trifluoromethyl-thiophenolato)aluminum]bis[μ-(4-trifluoromethyl-thiophenolato)]bis(trihexylphosphine)-silver; [bis(4-trifluoromethyl-thiophenolato)aluminum]bis[μ-(4-trifluoromethyl-thiophenolato)]bis(triphenylphosphine)-silver; [bis(4-trifluoromethyl-thiophenolato)aluminum]bis[μ-(4-trifluoromethyl-thiophenolato)]bis(perfluorotriphenylphosphine)-silver; [bis(3,5-bis(trifluoromethyl)-thiophenolato)aluminum]bis[μ-(3,5-bis(trifluoromethyl)-thiophenolato)]bis(triisobutylphosphine)-silver; [bis(3,5-bis(trifluoromethyl)-thiophenolato)

aluminum]bis[μ-(3,5-bis(trifluoromethyl)-thiophenolato)] bis(trihexylphosphine)-silver; [bis(3,5-bis(trifluoromethyl)-thiophenolato)aluminum]bis[μ-(3,5-bis(trifluoromethyl)-thiophenolato)]bis(triphenylphosphine)-silver; [bis(3,5-bis(trifluoromethyl)-thiophenolato) aluminum]bis[μ-(3,5-bis(trifluoromethyl)-thiophenolato)]bis(perfluorotriphenylphosphine)-silver; [bis(thiophenolato) aluminum]bis[μ-(thiophenolato)]bis(triisobutylphosphine)-silver; [bis(thiophenolato)aluminum]bis[μ-(thiophenolato)] bis(trihexylphosphine)-silver; [bis(thiophenolato) aluminum]bis[μ-(thiophenolato)]bis(triphenylphosphine)-silver; [bis(thiophenolato)aluminum]bis[μ-(thiophenolato)] bis(perfluorotriphenylphosphine)-silver; [bis(α-toluenethiolato)aluminum]bis[μ-(α-toluenethiolato)]bis(triisobutylphosphine)-silver; [bis(α-toluenethiolato) aluminum]bis[μ-(α-toluenethiolato)]bis(trihexylphosphine)-silver; [bis(α-toluenethiolato) aluminum]bis[μ-(α-toluenethiolato)]bis(triphenylphosphine)-silver; [bis(α-toluenethiolato) aluminum]bis[μ-(α-toluenethiolato)]bis(perfluorotriphenylphosphine)-silver; [bis(pentafluorothiophenolato)aluminum]bis[μ-(pentafluorothiophenolato)]bis (triisobutylphosphine)-silver; [bis(pentafluorothiophenolato)aluminum]bis[μ-(pentafluorothiophenolato)]bis(trihexylphosphine)-silver; [bis(pentafluorothiophenolato) aluminum]bis[μ-(pentafluorothiophenolato)]bis(triphenylphosphine)-silver; and [bis(pentafluorothiophenolato)aluminum]bis[μ-(pentafluorothiophenolato)]bis(perfluorotriphenylphosphine)-silver.

The examples of SSPs set forth above are examples only, and those of ordinary skill in the art will understand that such examples may be used to derive many other SSPs for use in forming chalcogenide materials such as, for example, ternary chalcopyrite materials.

Embodiments of the present invention include methods of forming SSPs. The methods are believed to be generally faster, more versatile (may be used to form a wider variety of SSPs), and to exhibit improved yield relative to other methods known in the art.

An example of a reaction pathway in accordance with some embodiments of the present invention is represented by Reactions 1 through 3 below:

In some embodiments of the present invention, SSPs of the general formula $L_2N(\mu\text{-}ER)_2M'(ER)_2$ may be formed using a reaction pathway in accordance with Reactions 1 through 3 below:

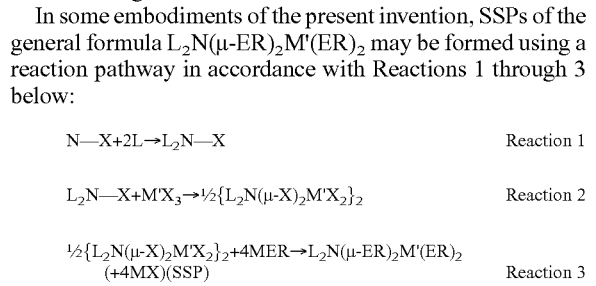

N—X+2L→L$_2$N—X     Reaction 1

L$_2$N—X+M'X$_3$→½{L$_2$N(μ-X)$_2$M'X$_2$}$_2$     Reaction 2

½{L$_2$N(μ-X)$_2$M'X$_2$}$_2$+4MER→L$_2$N(μ-ER)$_2$M'(ER)$_2$ (+4MX)(SSP)     Reaction 3 wherein L is a Lewis base (that is coordinated to N by a dative bond), each N is individually selected from Group IB atoms, each M is individually selected from Group IA atoms, each M' is individually selected from Group IIIA atoms, each E is individually selected from Group VIA atoms, each X is individually selected from Group VIIA atoms or a nitrate group, and each R group is individually selected from the group consisting of alkyl, aryl, vinyl, (per)fluoro alkyl, (per)fluoro aryl, silane, and carbamato groups. In accordance with some embodiments of the present invention, the Lewis base L may comprise, for example, a substituted phosphine of the general formula PR$_3$, wherein P is a phosphorous atom and each R is individually selected from the group consisting of alkyl, aryl, vinyl, (per)fluoro alkyl, (per)fluoro aryl, silane, and carbamato groups. As a non-limiting example, the Lewis base L may comprise a phosphine compound such as Ph$_3$P, wherein Ph is the phenyl group (a functional group comprising an aromatic cyclic ring of the formula C$_6$H$_5^-$). In accordance with additional embodiments of the present invention, the Lewis base L may comprise, for example, a substituted multidentate phosphine of the general formula R$_2$PAPR$_2$, wherein P is a phosphorous atom, each A is individually selected from the group consisting of alkyl, aryl, and vinyl, and each R is individually selected from the group consisting of alkyl, aryl, vinyl, (per)fluoro alkyl, (per)fluoro aryl, silane, and carbamato groups. As a non-limiting example, the Lewis base L may comprise a phosphine compound such as Ph$_2$PC$_6$H$_4$OC$_6$H$_4$PPh$_2$ (bis(2-diphenylphosphinophenyl) ether), wherein Ph is the phenyl group (a functional group comprising an aromatic cyclic ring of the formula C$_6$H$_5^-$).

Reactions 1 through 3 above, when combined and balanced, result in the net reaction N—X+2L+M'X$_3$+4MER→L$_2$N(μ-ER)$_2$M'(ER)$_2$ (+4MX). The particular reaction pathway prescribed by Reactions 1 through 3 results in the formation of the intermediate products L$_2$N—X and ½{L$_2$N(μ-X)$_2$M'X$_2$}$_2$. Such reaction pathways provide certain advantages over previously known methods of forming SSPs having the general formula L$_2$N(μ-ER)$_2$M'(ER)$_2$.

Referring to Reaction 1, a first reagent comprising L$_2$N—X (for use in Reaction 2) may be formed by reacting a Lewis base (e.g., a substituted phosphine (PR$_3$)) with a metal halide or nitride (N—X). The molar ratio of the Lewis base to the metal halide or nitride may be, for example, two (2) to one (1) (in other words, two molar equivalents of the Lewis base and one molar equivalent of the metal halide or nitride may be reacted with one another in Reaction 1), although the particular molar ratio may depend on the particular SSP to be formed.

Reaction 1 may be carried out in solution. For example, Reaction 1 may be performed in anhydrous benzene (C$_6$H$_6$), in acetonitrile (CH$_3$CN), in a mixture of more than one solvent, or in another suitable solvent. The product of Reaction 1 may comprise a suspension in which the first reagent comprising L$_2$N—X is present as a liquid or solid product suspended in the solution. The suspension may be concentrated to yield a liquid or a solid product comprising the L$_2$N—X substance. Alternatively, the reaction may be conducted in a single pot reaction, wherein the L$_2$N—X substance is not concentrated.

Referring to Reaction 2, the intermediate product ½{L$_2$N(μ-X)$_2$M'X$_2$}$_2$ may be formed by reacting the first reagent comprising L$_2$N—X with M'X$_3$. The molar ratio of the L$_2$N—X reagent to the M'X$_3$ reagent may be, for example, one (1) to one (1) (in other words, one molar equivalent of the L$_2$N—X reagent and one molar equivalent of the M'X$_3$ reagent may be reacted with one another in Reaction 2), although, again, the particular molar ratio may depend on the particular SSP to be formed.

Reaction 2 also may be carried out in solution. For example, Reaction 2 may be performed in the same benzene (C$_6$H$_6$) (or other solvent or solvent mixture) used in Reaction 1 or another suitable solvent (i.e., a solvent in which the L$_2$N—X reagent and/or the M'X$_3$ reagent is soluble). The product of Reaction 2 may comprise a solution or a suspension comprising the intermediate product ½{L$_2$N(μ-X)$_2$M'X$_2$}$_2$.

Referring to Reaction 3, an SSP of the general formula L$_2$N(μ-ER)$_2$M'(ER)$_2$ may be formed by reacting the intermediate product ½{L$_2$N(μ-X)$_2$M'X$_2$}$_2$ of Reaction 2 with the MER reagent. By way of example and not limitation, the MER reagent may be added to the solution or suspension that is the product of Reaction 2 and includes the intermediate product $\frac{1}{2}\{L_2N(\mu\text{-}X)_2M'X_2\}_2$. The molar ratio of the MER reagent to the $\frac{1}{2}\{L_2N(\mu\text{-}X)_2MX_2\}_2$ reagent may be, for example, four (4) to one (1) (in other words, four molar equivalents of the MER reagent and one molar equivalent of the $\frac{1}{2}\{L_2N(\mu\text{-}X)_2M'X_2\}_2$ reagent may be reacted with one another in Reaction 3), although, again, the particular molar ratio may depend on the particular SSP to be formed. It is noted that the R groups in the four molar equivalents of the MER reagent may differ from one another, and may be individually selected from the group consisting of alkyl, aryl, vinyl, (per)fluoro alkyl, (per)fluoro aryl, silane, and carbamato groups. In other words, one molar equivalent of the MER reagent may comprise $R^1$, one molar equivalent of the MER reagent may comprise $R^2$, one molar equivalent of the MER reagent may comprise $R^3$, and one molar equivalent of the MER reagent may comprise $R^4$, wherein $R^1$, $R^2$, $R^3$, and $R^4$ all differ from one another. In additional embodiments, less than four different R groups (e.g., one, two, or three), or more than four different R groups may be employed in the MER reagent. Similarly, the E groups in the four molar equivalents of the MER reagent may differ from one another, and may be individually selected from the Group VIA atoms. In other words, one molar equivalent of the MER reagent may comprise $E^1$, one molar equivalent of the MER reagent may comprise $E^2$, one molar equivalent of the MER reagent may comprise $E^3$, and one molar equivalent of the MER reagent may comprise $E^4$, wherein $E^1$, $E^2$, $E^3$, and $E^4$ all differ from one another. In additional embodiments, less than four different E groups (e.g., one, two, or three), or more than four different E groups may be employed in the MER reagent.

Reaction 3 also may be carried out in solution. For example, Reaction 3 may be performed in the same in the same benzene ($C_6H_6$) (or other solvent or solvent mixture) used in Reaction 2 or another suitable solvent, after carrying out Reaction 2, such that the solution includes the intermediate product and reagent $\frac{1}{2}\{L_2N(\mu\text{-}X)_2M'X_2\}_2$. The product of Reaction 3 may comprise a suspension in which the SSP of the general formula $L_2N(\mu\text{-}ER)_2M'(ER)_2$ is present as a liquid or solid product dissolved or suspended in the solution. The by-product may be filtered, and the filtrate may be concentrated to isolate the SSP. The SSP may comprise a liquid or solid product, and the solid SSP may be re-crystallized as desirable in preparation for utilizing the SSP to form a chalcogenide material (e.g., a ternary chalcopyrite material).

In accordance with some embodiments of the present invention, SSPs of the general formula $L_2N(\mu\text{-}E^1R^1)(\mu\text{-}E^2R^2)M'(E^2R^2)_2$ (SSP) or $L_2N(\mu\text{-}E^2R^2)_2M'(E^2R^2)(E^1R^1)$ (SSP) may be formed using reaction pathways in accordance with additional embodiments of the present invention represented by Reaction 1 (which is the same as above and repeated below for convenience) and Reactions 4 through 6 below:

$$N\text{—}X+2L \rightarrow L_2N\text{—}X \quad \text{Reaction 1}$$

$$L_2N\text{—}X+ME^1R^1 \rightarrow L_2N\text{-}E^1R^1(+MX) \quad \text{Reaction 4}$$

$$M'X_3+nME^2R^2 \rightarrow M'(E^2R^2)_n(+nMX) \quad \text{Reaction 5}$$

$$L_2N\text{-}E^1R^1+M'(E^2R^2)_n \rightarrow L_2N(\mu\text{-}E^1R^1)(\mu\text{-}E^2R^2)M'(E^2R^2)_2(\text{SSP}) \text{ or } L_2N(\mu\text{-}E^2R^2)_2M'(E^2R^2)(E^1R^1)(\text{SSP}) \quad \text{Reaction 6}$$

wherein L is a Lewis base (that is coordinated to N by a dative bond), each N is individually selected from Group IB atoms, each M is individually selected from Group IA atoms, each M' is individually selected from Group IIIA atoms, each $E^1$ and $E^2$ is individually selected from Group VIA atoms ($E^1$ and $E^2$ may be same or different), each X is individually selected from Group VIIA atoms or a nitrate group, n is any number (e.g., an integer) from one (1) to three (3), and each $R^1$ and $R^2$ group is individually selected from the group consisting of alkyl, aryl, vinyl, (per)fluoro alkyl, (per)fluoro aryl, silane, and carbamato groups, wherein at least one $E^1$ differs from at least one $E^2$ and/or at least one $R^1$ differs from at least one $R^2$. In some embodiments, each $E^1$ may differ from each $E^2$. In some embodiments, each $R^1$ may differ from each $R^2$.

Reaction 1 may be carried out as previously described herein. Referring to Reaction 4, the intermediate product $L_2N\text{-}E^1R^1$ may be formed by reacting the $L_2N\text{—}X$ (obtained by Reaction 1) with $ME^1R^1$. The molar ratio of the $L_2N\text{—}X$ reagent to the $ME^1R^1$ reagent may be, for example, one (1) to one (1) (in other words, one molar equivalent of the $L_2N\text{—}X$ reagent and one molar equivalent of the $ME^1R^1$ reagent may be reacted with one another in Reaction 4), although, again, the particular molar ratio may depend on the particular SSP to be formed.

Reaction 4 also may be carried out in solution. For example, Reaction 4 may be performed in the same benzene ($C_6H_6$) or other solution used in Reaction 1, or in another suitable solvent (i.e., a solvent in which the $L_2N\text{—}X$ reagent and/or the $ME^1R^1$ reagent is soluble). The product of Reaction 4 may comprise a solution or a suspension comprising the intermediate product $L_2N\text{-}E^1R^1$.

Referring to Reaction 5, the intermediate product $M'(E^2R^2)_n$ may be formed by reacting $M'X_3$ with $ME^2R^2$. The molar ratio of the $M'X_3$ reagent to the $ME^2R^2$ reagent may be, for example, one (1) to three (3) (in other words, one molar equivalent of the $M'X_3$ reagent and three molar equivalents of the $ME^2R^2$ reagent may be reacted with one another in Reaction 5), although, again, the particular molar ratio may depend on the particular SSP to be formed.

Reaction 5 also may be carried out in solution. For example, Reaction 5 may be performed in the same benzene ($C_6H_6$) or other solution (i.e., a solvent in which the $M'X_3$ reagent and/or the $ME^2R^2$ reagent is soluble). The product of Reaction 5 may comprise a solution or a suspension comprising the intermediate products $M'(E^2R^2)_n$. It is noted that the $R^2$ groups in the four molar equivalents of the $ME^2R^2$ reagent may be individually selected from the group consisting of alkyl, aryl, vinyl, (per)fluoro alkyl, (per)fluoro aryl, silane, and carbamato groups. Thus, each of the $R^2$ groups may be the same or they may differ from one another. Similarly, the $E^2$ groups in the four molar equivalents of the $ME^2R^2$ reagent may be individually selected from the Group VIA atoms, and, thus, may be the same or they may differ from one another.

Referring to Reaction 6, an SSP of the general formula $L_2N(\mu\text{-}E^1R^1)(\mu\text{-}E^2R^2)M'(E^2R^2)_2$ or $L_2N(\mu\text{-}E^2R^2)_2M'(E^1R^1)(E^2R^2)$ may be formed by reacting the intermediate product $L_2N\text{-}E^1R^1$ of Reaction 4 with the intermediate product $M'(E^2R^2)_n$ of Reaction 5. By way of example and not limitation, the intermediate product $M'(E^2R^2)_n$ may be added to the solution or suspension that is the product of Reaction 4 and includes the intermediate product $L_2N\text{-}E^1R^1$. The molar ratio of the $L_2N\text{-}E^1R^1$ reagent to the $M'(E^2R^2)_n$ reagent may be, for example, one (1) to one (1) (in other words, one molar equivalent of the $L_2N\text{-}E^1R^1$ reagent and one molar equivalent of the $M'(E^2R^2)_n$ reagent may be reacted with one another in Reaction 6), although, again, the particular molar ratio may depend on the particular SSP to be formed.

Reaction 6 also may be carried out in solution. For example, Reaction 6 may be performed in the same benzene ($C_6H_6$) or other solution used in Reaction 5, after carrying out Reaction 5, such that the solution includes the intermediate product and reagent $M'(E^2R^2)$. The product of Reaction 6 may comprise a suspension in which the SSP of the general formula $L_2N(\mu\text{-}E^1R^1)(\mu\text{-}E^2R^2)M'(E^2R^2)_2$ or $L_2N(\mu\text{-}E^2R^2)_2M'(E^1R^1)(E^2R^2)$ is present as a liquid or solid dissolved or suspended in the solution. The by-product may be filtered, and the filtrate may be concentrated to isolate the SSP. The SSP may comprise a liquid or solid product, and the solid SSP may be re-crystallized as desirable in preparation for utilizing the SSP to form a chalcogenide material (e.g., a ternary chalcopyrite material).

In accordance some embodiments of the present invention, SSPs of the general formula $L_2N(\mu\text{-}ER^1)(\mu\text{-}ER^2)M'(ER^3)(ER^4)$ may be formed using Reactions 1 and 4 (which are the same as above and repeated below for convenience) and Reactions 7 through 10 below:

$$N-X+2L \rightarrow L_2N-X \quad \text{Reaction 1}$$

$$L_2N-X+MER^1 \rightarrow L_2N\text{-}ER^1(+MX) \quad \text{Reaction 4}$$

$$L_2N\text{-}ER^1+M'X_3 \rightarrow L_2N(\mu\text{-}ER^1)(\mu\text{-}X)M'X_2 \quad \text{Reaction 7}$$

$$L_2N(\mu\text{-}ER^1)(\mu\text{-}X)M'X_2+MER^2 \rightarrow L_2N(\mu\text{-}ER^1)(\mu\text{-}ER^2)M'X_2(+MX) \quad \text{Reaction 8}$$

$$L_2N(\mu\text{-}ER^1)(\mu\text{-}ER^2)M'X_2+MER^3 \rightarrow L_2N(\mu\text{-}ER^1)(\mu\text{-}ER^2)M'(ER^3)X(+MX) \quad \text{Reaction 9}$$

$$L_2N(\mu\text{-}ER^1)(\mu\text{-}ER^2)M'(ER^3)X+MER^4 \rightarrow L_2N(\mu\text{-}ER^1)(\mu\text{-}ER^2)M'(ER^3)(ER^4)(+MX)(SSP) \quad \text{Reaction 10}$$

wherein L is a Lewis base that is coordinated to N by a dative bond, each N is individually selected from Group IB atoms, each M is individually selected from Group IA atoms, each M' is individually selected from Group IIIA atoms, each E is individually selected from Group VIA atoms, each X is individually selected from Group VIIA atoms or a nitrate group, each R', $R^2$, $R^3$, and $R^4$ group is individually selected from the group consisting of alkyl, aryl, vinyl, (per)fluoro alkyl, (per)fluoro aryl, silane, and carbamato groups, and R', $R^2$, $R^3$, $R^4$ are different from one another. The E groups in the $MER^1$, $MER^2$, $MER^3$, and $MER^4$ reagents may be the same or they may be different from one another. In other words, the $MER^1$ reagent may comprise $E^1$, the $MER^2$ reagent may comprise $E^2$, the $MER^3$ reagent may comprise $E^3$, and the $MER^4$ reagent may comprise $E^4$, wherein $E^1$, $E^2$, $E^3$, and $E^4$ all differ from one another. In additional embodiments, less than four different E groups (e.g., one, two, or three), or more than four different E groups may be employed in the $MER^1$, $MER^2$, $MER^3$, and $MER^4$ reagents.

Reactions 1 and 4 may be carried out as previously described herein.

Referring to Reaction 7, the intermediate product $L_2N(\mu\text{-}ER^1)(\mu\text{-}X)M'X_2$ (which may be an SSP) may be formed by reacting the $L_2N\text{-}ER^1$ (obtained by Reaction 4) with $M'X_3$. The molar ratio of the $L_2N\text{-}ER^1$ reagent to the $M'X_3$ reagent may be, for example, one (1) to one (1) (in other words, one molar equivalent of the $M'X_3$ reagent and one molar equivalent of the $L_2N\text{-}ER^1$ reagent may be reacted with one another in Reaction 7). Reaction 7 may be carried out in a solution such as benzene ($C_6H_6$) or in another suitable solvent or mixture of solvents. The product of Reaction 7 may comprise a solution or a suspension comprising the intermediate SSP product $L_2N(\mu\text{-}ER^1)(\mu\text{-}X)M'X_2$.

Referring to Reaction 8, the intermediate SSP product $L_2N(\mu\text{-}ER^1)(\mu\text{-}ER^2)M'X_2$ may be formed by reacting one (1) molar equivalent of $MER^2$ with the intermediate SSP product $L_2N(\mu\text{-}ER^1)(\mu\text{-}X)M'X_2$ of Reaction 7. As shown in Reaction 9, the intermediate SSP product $L_2N(\mu\text{-}ER^1)(\mu\text{-}ER^2)M'(ER^3)X$ may be formed by reacting one (1) molar equivalent of $MER^3$ with one (1) molar equivalent of the SSP intermediate product $L_2N(\mu\text{-}ER^1)(\mu\text{-}ER^2)M'X_2$ obtained by Reaction 8. Similarly, as shown in Reaction 10, a final SSP product of the general formula $L_2N(\mu\text{-}ER^1)(\mu\text{-}ER^2)M'(ER^3)(ER^4)$ may be formed by reacting one (1) molar equivalent of $MER^4$ with one (1) molar equivalent of the SSP intermediate product $L_2N(\mu\text{-}ER^1)(\mu\text{-}ER^2)M'(ER^3)X$ obtained by Reaction 9. The product of Reaction 10 may comprise a suspension in which an SSP of the general formula $L_2N(\mu\text{-}ER^1)(\mu\text{-}ER^2)M'(ER^3)(ER^4)$ is present as a liquid or solid dissolved or suspended in the solution. It is noted that the various groups may not be added to the particular positions of the SSP in the order represented above, and, thus, the $ER^1$, $ER^2$, $ER^3$, and $ER^4$ groups may be in any position in the SSP. The by-product may be filtered, and the filtrate may be concentrated to isolate the SSP. The SSP may comprise a liquid or solid product, and the solid SSP may be re-crystallized as desirable in preparation for utilizing the SSP to form a chalcogenide material (e.g., a ternary chalcopyrite material).

In accordance with additional embodiments of the present invention, after forming SSPs as previously described herein, the composition of the SSPs may be tailored by carrying out one or more additional reactions (e.g., substitution reactions) with the SSPs, as described below. For example, after forming a first SSP(SSP'), a second, different SSP ($SSP^2$) of the general formula $L_2N(\mu\text{-}E^1R^1)(\mu\text{-}E^2R^2)M'(E^3R^3)(E^4R^4)$ may be formed from the first $SSP^1$ in accordance with Reaction 11 below:

$$SSP^1+nHE^1R^1+mHE^2R^2+oHE^3R^3+pHE^4R^4 \rightarrow L_2N(\mu\text{-}E^1R^1)(\mu\text{-}E^2R^2)M'(E^3R^3)(E^4R^4)(SSP) \quad \text{Reaction 11}$$

wherein each of n, m, o, and p is any number between zero (0) and four (4), the sum of n, m, o, and p is four (4), L is a Lewis base that is coordinated to N by a dative bond, each N is individually selected from Group IB atoms, each M' is individually selected from Group IIIA atoms, each of $E^1$, $E^2$, $E^3$, and $E^4$ is individually selected from Group VIA atoms, each of $R^1$, $R^2$, $R^3$, and $R^4$ is individually selected from the group consisting of alkyl, aryl, vinyl, (per)fluoro alkyl, (per)fluoro aryl, silane, and carbamato groups. In Reaction 11, $R^1$, $R^2$, $R^3$, and $R^4$ may be the same or different from one another, and $E^1$, $E^2$, $E^3$, and $E^4$ may be the same or different from one another.

As one non-limiting example, after forming an SSP of the general formula $L_2N(\mu\text{-}ER)_2M'(ER)_2$ using Reactions 1 through 3, as previously described, a different SSP of the general formula $L_2N(\mu\text{-}E^1R^1)_2M'(E^1R^1)_2$ may be formed from the SSP in accordance with Reaction 11 by reacting four (4) molar equivalents of $HE^1R^1$ with one (1) molar equivalent of the $L_2N(\mu\text{-}E^1R^1)_2M'(E^1R^2)$SSP. As another non-limiting example, after forming an SSP of the general formula $L_2N(\mu\text{-}E^1R^1)(\mu\text{-}E^2R^2)M'(E^2R^2)_2$ using Reactions 1, 4, 5, and 6, as previously described, a different SSP of the general formula $L_2N(\mu\text{-}E^3R^3)_2M'(E^3R^3)_2$ may be formed from the SSP in accordance with Reaction 11 by reacting four (4) molar equivalents of $HE^3R^3$ with one (1) molar equivalent of the $L_2N(\mu\text{-}E^1R^1)(\mu\text{-}E^2R^2)M'(E^2R^2)$ SSP. As yet another non-limiting example, after forming an SSP of the general formula $L_2N(\mu\text{-}ER^1)(\mu\text{-}ER^2)M'(ER^3)(ER^4)$ using Reactions 1, 4, and 7 through 10, as previously described, a different SSP of the general formula $L_2N(\mu\text{-}E^2R^5)_2M'(E^2R^5)_2$ may be formed from the SSP in accordance with Reaction 11 by reacting four (4) molar equivalents of $HE^2R^5$ with one (1) molar equivalent of the $L_2N(\mu\text{-}ER^1)(\mu\text{-}ER^2)M'(ER^3)(ER^4)$ SSP.

Reaction 11 also may be carried out in solution. For example, Reaction 11 may be performed in benzene ($C_6H_6$) or another suitable solvent or solvent mixture. The product of Reaction 11 may comprise a suspension in which the SSP product is present as liquid or solid matter dissolved or suspended in the solution. The by-product may be filtered, and the filtrate may be concentrated to isolate the SSP product. The SSP product may comprise a liquid or solid product, and the solid SSP may be re-crystallized as desirable in preparation for utilizing the SSP to form a chalcogenide material (e.g., a ternary chalcopyrite material).

The reaction mechanisms described hereinabove with reference to Reactions 1 through 11 may be used to form a wide variety of SSPs. For example, different species of the $L_2N$—X reagent (Reaction 2) and the ME'R$^1$ reagent (Reaction 3) may be used to place different R$^1$ groups on the SSPs, different E$^1$ groups on the SSPs, or different L groups on the SSPs, and different species of the $L_2N$—X reagent, the M'X$_3$ reagent, and the ME$^1$R$^1$ reagent may be used in selected ratios to tailor the identity and concentration of the N, M', and E atoms in the SSPs. Four non-limiting examples of embodiments of the present invention are set forth below to illustrate the versatility in forming SSPs in accordance with embodiments of the present invention. Embodiments of the present invention, however, are not to be limited to methods of forming the specific SSPs formed in the examples below, or to methods employing the particular reagents employed in the examples below.

EXAMPLE 1

The SSP $(Ph_3P)_2Cu(\mu\text{-SEt})_2In(SEt)_2$ may be formed as follows.

Two (2) molar equivalents of $Ph_3P$ (42.000 grams, 160.13 millimoles) may be added to a mixture of two hundred forty (240) milliliters (mL) of anhydrous benzene ($C_6H_6$) and two hundred forty (240) milliliters (mL) of anhydrous tetrahydrofuran (($CH_2)_4O$, THF) to form a first solution, which may be stirred. One (1) molar equivalent of anhydrous Cu(I)Cl (7.9260 grams, 80.064 millimoles) may be added to the stirring first solution to form a first white suspension including the intermediate product $(Ph_3P)_2Cu$—Cl. The first suspension may be concentrated to form a solid product or kept to continue the reaction as a one pot reaction, which is referred to herein as "Mixture A."

A second solution may be formed by adding 1.4770 molar equivalents of KH (40.000 grams, 299.18 millimoles, collected from thirty (30) weight percent dispersion in mineral oil and washed several times with benzene) to about 100 mL of benzene. One (1) molar equivalent of EtSH (15.000 mL, 202.56 millimoles) (Et is the ethyl group) may be added to the second solution and stirred for a few minutes. The EtSH and the KH react with one another to form KSEt. The resulting product that includes the KSEt (which may comprise a solution or a solid product comprising the KSEt formed by drying a solution) is referred to herein as "Mixture B."

A "Mixture C" may also be formed by adding one (1) molar equivalent of Na metal (34.000 grams, 1478.9 millimoles, collected from mineral oil and washed several times with diethyl ether) to about 500 mL of diethyl ether. One (1) molar equivalent of EtSH (109.52 mL, 1478.9 millimoles) may be added to the second solution and stirred for twelve (12) hours at forty (40) degrees Celsius (° C.). The EtSH and the Na metal react with one another to form NaSEt. The resulting product that includes the NaSEt (which may comprise a solution or a solid product comprising the NaSEt formed by drying a solution) is Mixture C.

If the reaction is a one pot reaction, one (1) molar equivalent of anhydrous InCl$_3$ (17.709 grams, 80.064 millimoles) may be added to Mixture A, after which this third solution may be stirred for about sixty (60) minutes at eighty (80) degrees Celsius (° C.). The resulting mixture may comprise a fourth solution. This solution may comprise the intermediate product $\{(Ph_3P)_2Cu(\mu\text{-Cl})_2InCl_2\}_2$, a computer generated graphical representation of which is illustrated in FIG. 1. As shown in FIG. 1, this intermediate product comprises an eight (8) member ring structure defined by two (2) copper atoms, two (2) indium atoms, and four (4) chlorine atoms.

Four (4) molar equivalents of NaSEt (26.940 grams, 320.26 millimoles) or KSEt (32.100 grams, 320.26 millimoles) provided by Mixture B or C, respectively, may be added to the fourth solution and stirred for an additional twelve (12) hours at eighty (80)° C.

Figure 2:
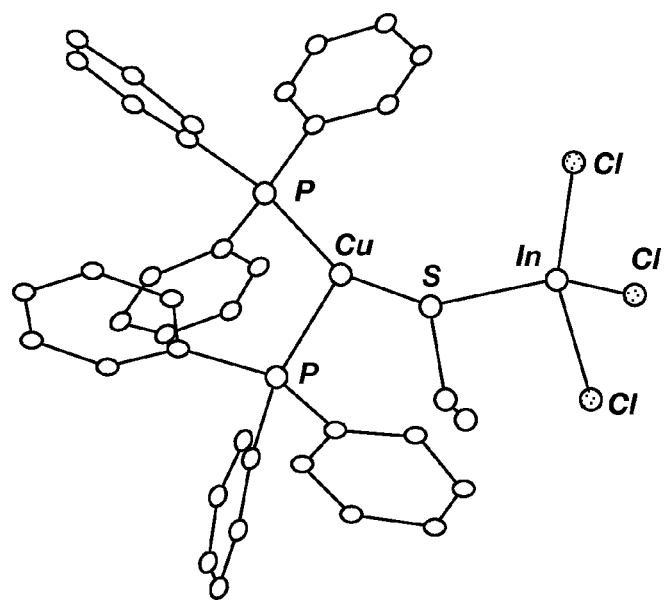
Figure 3:
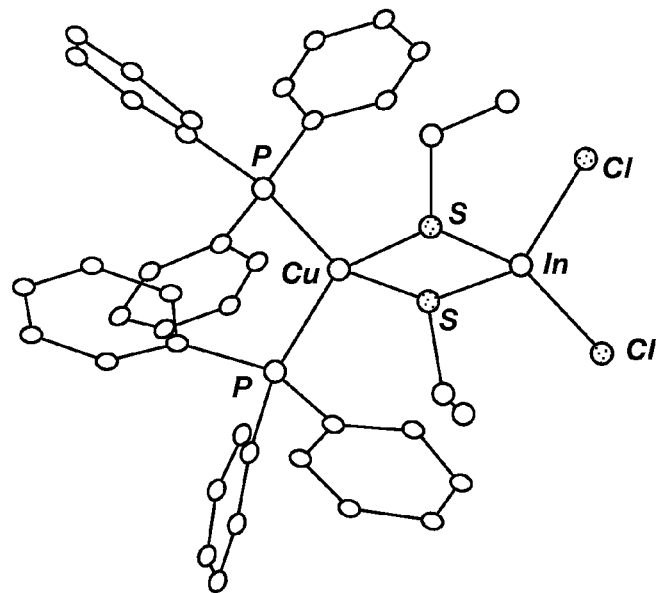
Figure 4:
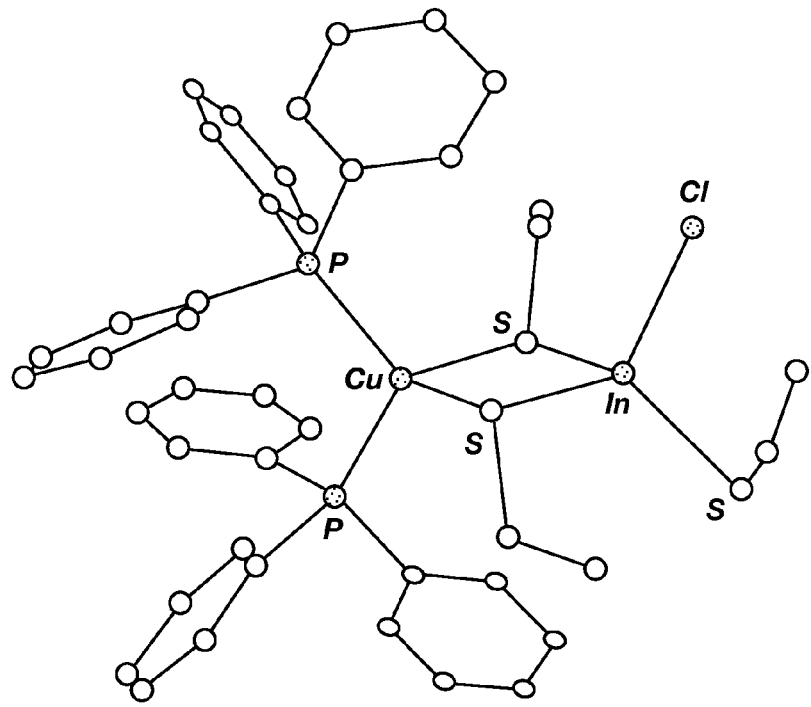
Figure 5:
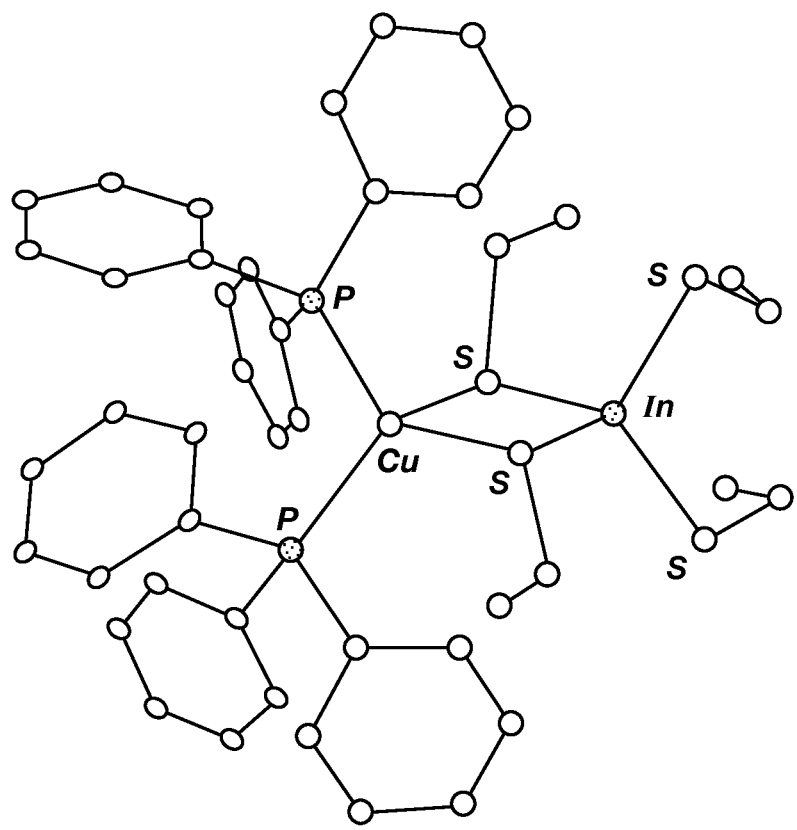
FIG. 5 illustrates one example of a single source precursor that may be formed using methods of the present invention.

In some embodiments, however, less than four (4) molar equivalents of the NaSEt or KSEt may initially be added to the fourth solution. Fractions of the four (4) molar equivalents may be added sequentially to attain various intermediate products. For example, one (1) molar equivalent of the NaSEt or KSEt may initially be added to the fourth solution to form an intermediate product, the exact nature of which is not known, but is currently believed to be the $(Ph_3P)_2Cu(\mu\text{-SEt})$ InCl$_3$ species shown in the computer generated graphical representation of FIG. 2. A second molar equivalent of the NaSEt or KSEt may be added to the fourth solution to form another intermediate product, the exact nature of which is not known, but is currently believed to be the $(Ph_3P)_2Cu(\mu\text{-SEt})_2$ InCl$_2$ species shown in the computer generated graphical representation of FIG. 3. Similarly, a third molar equivalent of the NaSEt or KSEt may then be added to the fourth solution to form another intermediate product, the exact nature of which is not known, but is currently believed to be the $(Ph_3P)_2$ Cu($\mu$-SEt)$_2$In(SEt)Cl species shown in the computer generated graphical representation of FIG. 4. Finally, a fourth molar equivalent of the NaSEt may be added to the fourth solution to form the final SSP product $(Ph_3P)_2Cu(\mu\text{-SEt})_2In$ $(SEt)_2$, which is shown in the computer generated graphical representation of FIG. 5.

After all four (4) molar equivalents of the NaSEt or KSEt provided by Mixture B or C, respectively, have been added to the fourth solution, the solution may be stirred for an additional twelve (12) hours at eighty degrees Celsius (80° C.). After stirring, the resulting mixture may comprise a suspension that includes a solution with particles of the SSP $(Ph_3P)_2$ Cu($\mu$-SEt)$_2$In(SEt)$_2$ suspended therein. The SSP may be isolated by filtering of by-product, and the filtrate may be concentrated as necessary or desirable. Optionally, the isolated SSP may be re-crystallized in preparation for using the SSP to form the ternary chalcopyrite material CuInS$_2$.

It will be apparent from the above description that, in additional embodiments, instead of using the same reagent (e.g., NaSEt) in each of the sequential additions to the reaction mixture, different reagents including different moieties (other than ethyl groups) may be added to the fourth solution to substitute different, selected moieties into the resulting SSP product at different selected locations within the structure of the SSP molecule or complex.

EXAMPLE 2

The SSP $(Ph_3P)_2Cu(t\text{-SBn})(\mu\text{-SEt})Ga(SEt)_2$ may be formed as follows.

The intermediate product $(Ph_3P)_2Cu$—Cl is formed as described in Example 1 above (and repeated below for convenience). Two (2) molar equivalents of Ph$_3$P (42.000 grams, 160.13 millimoles) may be added to mixture of two hundred forty (240) milliliters (mL) of anhydrous benzene (C$_6$H$_6$) and two hundred forty (240) milliliters (mL) of anhydrous tetrahydrofuran (($CH_2)_4O$, THF) to form a first solution, which may be stirred. One (1) molar equivalent of anhydrous Cu(I) Cl (7.9260 grams, 80.064 millimoles) may be added to the stirring first solution to form a first white suspension including the intermediate product $(Ph_3P)_2Cu$—Cl. The first suspension may be concentrated to form a solid product or kept to continue the reaction, which is referred to herein as "Mixture A."

A second solution (which is the same as above and repeated below for convenience) may be formed by adding one (1) molar equivalent of Na metal (34.000 grams, 1478.9 millimoles, collected from mineral oil and washed several times with diethyl ether) to about 500 mL of diethyl ether. One (1) molar equivalent of EtSH (109.52 mL, 1478.9 millimoles) may be added to the second solution and stirred for twelve (12) hours at forty (40) degrees Celsius (° C.). The EtSH and the Na metal react with one another to form NaSEt. The resulting product that includes the NaSEt (which may comprise a solution or a solid product comprising the NaSEt formed by drying a solution) is referred to herein as "Mixture B."

A third solution may be formed by adding one (1) molar equivalent of Na metal (10.000 grams, 434.97 millimoles, collected from mineral oil and washed several times with diethyl ether) to about 200 mL of diethyl ether. One (1) molar equivalent of $C_6H_5CH_2SH$ (HSBn, 51.066 mL, 434.97 millimoles) may be added to the third solution and stirred for twelve (12) hours at 40° C. The $C_6H_5CH_2SH$ and the Na metal react with one another to form $NaSCH_2C_6H_5$ (NaSBn). The resulting product that includes the NaSBn (which may comprise a solution or a solid product comprising the NaSBn formed by drying a solution) is referred to herein as "Mixture C."

A fourth solution may be formed by adding one (1) molar equivalent of $(Ph_3P)_2Cu$—Cl (49.926 grams, 80.064 millimoles) provided by Mixture A to about 200 mL of benzene. One (1) molar equivalent of NaSBn (8.1840 grams, 80.064 millimoles) provided by Mixture C may be added to the fourth solution and stirred for twelve (12) hours. The $(Ph_3P)_2Cu$—Cl and the NaSBn react with one another to form $(Ph_3P)_2CuSBn$. The resulting mixture may comprise a fourth solution. This solution may comprise the intermediate product $(Ph_3P)_2CuSBn$ (which may comprise a solution or a solid product comprising the $(Ph_3P)_2CuSBn$ formed by drying a solution) is referred to herein as "Mixture D."

A fifth solution may be formed by adding three (3) molar equivalents of NaSEt (20.205 grams, 240.192 millimoles) provided by Mixture B to about 200 mL of benzene. One (1) molar equivalent of anhydrous $GaCl_3$ (14.098 grams, 80.064 millimoles) may be added to this fifth solution, after which the fifth solution may be stirred for about sixty (60) minutes at eighty (80)° C. The resulting mixture may comprise a fifth solution. This solution may comprise the intermediate product $Ga(SEt)_3$ (which may comprise a solution or a solid product comprising the $Ga(SEt)_3$ formed by drying a solution).

One (1) molar equivalent of $(Ph_3P)_2CuSBn$ (56.950 grams, 80.064 millimoles) provided by Mixture D may be added to the fifth solution and stirred for an additional twelve (12) hours at eighty (80)° C. After stirring, the resulting mixture may comprise a suspension that includes a solution with particles of the SSP $(Ph_3P)_2Cu(\mu\text{-SBn})(\mu\text{-SEt})Ga(SEt)_2$ suspended therein. The SSP may be isolated by filtering of by-product, and the filtrate may be concentrated as necessary or desirable. Optionally, the isolated SSP may be re-crystallized in preparation for using the SSP to form the ternary chalcopyrite material $CuGaS_2$.

In some embodiments, however, less than three (3) molar equivalents of the NaSEt may initially be added to the fifth solution. Fractions of the three (3) molar equivalents may be added sequentially to attain various intermediate products. For example, one (1) molar equivalent of the NaSEt may initially be added to the fifth solution to form an intermediate product $GaSEtCl_2$. A second molar equivalent of the NaSEt may be added to the fifth solution to form another intermediate product $Ga(SEt)_2Cl$. Finally, a third molar equivalent of the NaSEt may then be added to the fifth solution to form another intermediate product $Ga(SEt)_3$.

It will be apparent from the above description that, in additional embodiments, instead of using the same reagent (e.g., NaSEt) in each of the sequential additions to the reaction mixture, different reagents including different moieties (other than ethyl groups) may be added to the fourth solution to substitute different, selected moieties into the resulting SSP product at different selected locations within the structure of the SSP molecule or complex.

EXAMPLE 3

The SSP $(Ph_3P)_2Cu(\mu\text{-SBn})(\mu\text{-SPh})Al(SEt)(SHex)$ may be formed as follows.

The intermediate product $(Ph_3P)_2Cu$—Cl is formed as described in Example 1 above (and repeated below for convenience). Two (2) molar equivalents of $Ph_3P$ (42.000 grams, 160.13 millimoles) may be added to a mixture of two hundred forty (240) milliliters (mL) of anhydrous benzene ($C_6H_6$) and two hundred forty (240) milliliters (mL) of anhydrous tetrahydrofuran (($CH_2)_4O$, THF) to form a first solution, which may be stirred. One (1) molar equivalent of anhydrous Cu(I) Cl (7.9260 grams, 80.064 millimoles) may be added to the stirring first solution to form a first white suspension including the intermediate product $(Ph_3P)_2Cu$—Cl. The first suspension may be concentrated to form a solid product or kept to continue the reaction, which is referred to herein as "Mixture A."

A second solution (which is formed as described above and repeated below for convenience) may be formed by adding one (1) molar equivalent of Na metal (34.000 grams, 1478.9 millimoles, collected from mineral oil and washed several times with diethyl ether) to about 500 mL of diethyl ether. One (1) molar equivalent of EtSH (109.52 mL, 1478.9 millimoles) may be added to the second solution and stirred for twelve (12) hours at forty (40) degrees Celsius (° C.). The EtSH and the Na metal react with one another to form NaSEt. The resulting product that includes the NaSEt (which may comprise a solution or a solid product comprising the NaSEt formed by drying a solution) is referred to herein as "Mixture B."

A third solution (which is formed as described above and repeated below for convenience) may be formed by adding one (1) molar equivalent of Na metal (10.000 grams, 434.97 millimoles, collected from mineral oil and washed several times with diethyl ether) to about 200 mL of diethyl ether. One (1) molar equivalent of $C_6H_5CH_2SH$ (HSBn, 51.066 mL, 434.97 millimoles) may be added to the third solution and stirred for twelve (12) hours at forty (40) degrees Celsius (° C.). The $C_6H_5CH_2SH$ and the Na metal react with one another to form $NaSCH_2C_6H_5$ (NaSBn). The resulting product that includes the NaSBn (which may comprise a solution or a solid product comprising the NaSBn formed by drying a solution) is referred to herein as "Mixture C."

A fourth solution may be formed by adding one (1) molar equivalent of Na metal (10.000 grams, 434.97 millimoles, collected from mineral oil and washed several times with diethyl ether) to about 200 mL of diethyl ether. One (1) molar equivalent of $C_6H_5SH$ (HSPh, 44.454 mL, 434.97 millimoles) may be added to the fourth solution and stirred for twelve (12) hours at forty (40) degrees Celsius (° C.). The $C_6H_5SH$ and the Na metal react with one another to form $NaSC_6H_5$ (NaSPh). The resulting product that includes the NaSPh (which may comprise a solution or a solid product comprising the NaSPh formed by drying a solution) is referred to herein as "Mixture D."

A fifth solution may be formed by adding one (1) molar equivalent of Na metal (10.000 grams, 434.97 millimoles, collected from mineral oil and washed several times with diethyl ether) to about 200 mL of diethyl ether. One (1) molar equivalent of $C_6H_{13}SH$ (HSHex, 61.227 mL, 434.972 millimoles) may be added to the fifth solution and stirred for twelve (12) hours at forty (40) degrees Celsius (° C.). The $C_6H_{13}SH$ and the Na metal react with one another to form $NaSC_6H_{13}$ (NaSHex). The resulting product that includes the NaSHex (which may comprise a solution or a solid product comprising the NaSHex formed by drying a solution) is referred to herein as "Mixture E."

A sixth solution may be formed by adding one (1) molar equivalent of NaSBn (8.184 grams, 80.064 millimoles) provided by Mixture C to the first solution (($Ph_3P)_2Cu$—Cl) provided by Mixture A, after which the sixth solution may be stirred for twelve (12) hours. The $(Ph_3P)_2Cu$—Cl and the NaSBn react with one another to form $(Ph_3P)_2CuSBn$. The resulting mixture may comprise a sixth solution. This solution may comprise the intermediate product $(Ph_3P)_2CuSBn$ (which may comprise a solution or a solid product comprising the $(Ph_3P)_2CuSBn$ formed by drying a solution) and is referred to herein as "Mixture F."

A seventh solution may be formed by adding one (1) molar equivalent anhydrous $AlCl_3$ (10.676 grams, 80.064 millimoles) to the sixth solution of $(Ph_3P)_2CuSBn$ provided by Mixture F, after which the seventh solution may be stirred for about sixty (60) minutes at eighty (80) degrees Celsius (° C.). The resulting mixture is the seventh solution. This solution may comprise the intermediate product $(Ph_3P)_2Cu(\mu\text{-}SBn)(\mu\text{-}Cl)Al(Cl)_2$ (which may comprise a solution or a solid product comprising the $(Ph_3P)_2Cu(\mu\text{-}SBn)(\mu\text{-}Cl)Al(Cl)_2$ formed by drying a solution) and is referred to herein as "Mixture G."

An eighth solution may be formed by adding one (1) molar equivalent NaSPh (10.581 grams, 80.064 millimoles) provided by Mixture D to the seventh solution of $(Ph_3P)_2Cu(\mu\text{-}SBn)(\mu\text{-}Cl)Al(Cl)_2$ provided by Mixture G, after which the eighth solution may be stirred for about sixty (60) minutes at eighty (80) degrees Celsius (° C.). The resulting mixture is the eighth solution. This solution may comprise the intermediate product $(Ph_3P)_2Cu(\mu\text{-}SBn)(\mu\text{-}SPh)Al(Cl)_2$ (which may comprise a solution or a solid product comprising the $(Ph_3P)_2Cu(\mu\text{-}SBn)(\mu\text{-}SPh)Al(Cl)_2$ formed by drying a solution) and is referred to herein as "Mixture H."

A ninth solution may be formed by adding one (1) molar equivalent NaSEt (6.735 grams, 80.064 millimoles) provided by Mixture B to the eighth solution of $(Ph_3P)_2Cu(\mu\text{-}SBn)(\mu\text{-}SPh)Al(Cl)_2$ provided by Mixture H, after which the ninth solution may be stirred for about sixty (60) minutes at eighty (80) degrees Celsius (° C.). The resulting mixture is the ninth solution. This solution may comprise the intermediate product $(Ph_3P)_2Cu(\mu\text{-}SBn)(\mu\text{-}SPh)Al(SEQ(Cl)$ (which may comprise a solution or a solid product comprising the $(Ph_3P)_2Cu(\mu\text{-}SBn)(\mu\text{-}Ph)Al(SEt)(Cl)$ formed by drying a solution) is referred to herein as "Mixture I."

A tenth solution may be formed by adding one (1) molar equivalent NaSHex (11.227 grams, 80.064 millimoles) provided by Mixture E to the ninth solution of $(Ph_3P)_2Cu(\mu\text{-}SBn)(\mu\text{-}SPh)Al(SEt)(Cl)$ provided by Mixture I, after which the tenth solution may be stirred for about twelve (12) hours at eighty (80) degrees Celsius (° C.). After stirring, the resulting mixture may comprise a suspension that includes a solution with particles of the SSP $(Ph_3P)_2Cu(\mu\text{-}SBn)(\mu\text{-}SPh)Al(SEt)(SHex)$ suspended therein. The SSP may be isolated by filtering of by-product, and the filtrate may be concentrated as necessary or desirable. Optionally, the isolated SSP may be re-crystallized in preparation for using the SSP to form the ternary chalcopyrite material $CuAlS_2$.

EXAMPLE 4

The SSP $(Ph_3P)_2Cu(\mu\text{-}SePh)_2In(SePh)_2$ may be formed as follows.

One (1) molar equivalent of the SSP $(Ph_3P)_2Cu(\mu\text{-}SEt)_2In(SEt)_2$ (10.000 grams, 10.555 millimoles), which may be formed as described in Example 1, may be added to about 50 mL of benzene to form a first solution, which may be stirred. Four (4) molar equivalents of $C_6H_5SeH$ (PhSeH, 4.7080 mL, 42.220 millimoles) may be added to the stirring first solution to form a first solution or suspension including the product $(Ph_3P)_2Cu(\mu\text{-}SePh)_2In(SePh)_2$. The first solution or suspension may be concentrated to form a liquid or solid product (or kept to continue the reaction as one pot reaction).

In some embodiments, however, less than four (4) molar equivalents of the PhSeH may initially be added to the first solution. Fractions of the four (4) molar equivalents may be added sequentially to attain various products. For example, one (1) molar equivalent of the PhSeH may initially be added to the first solution to form an intermediate product, the exact nature of which is not known, but is currently believed to be the $(Ph_3P)_2Cu(\mu\text{-}SEt)(uSePh)In(SEt)_2$ species. A second molar equivalent of the PhSeH may be added to the first solution to form another intermediate product, the exact nature of which is not known, but is currently believed to be the $(Ph_3P)_2Cu(\mu\text{-}SePh)_2In(SEt)_2$ species. Similarly, a third molar equivalent of the PhSeH may then be added to the first solution to form another intermediate product, the exact nature of which is not known, but is currently believed to be the $(Ph_3P)_2Cu(\mu\text{-}SePh)_2In(PhSe)(SEt)$ species. Finally, a fourth molar equivalent of the PhSeH may be added to the first solution to form the final SSP product $(Ph_3P)_2Cu(\mu\text{-}SePh)_2In(SePh)_2$.

After all four (4) molar equivalents of the PhSeH have been added to the first solution, the solution may be stirred for an additional one (1) hour. After stirring, the resulting mixture may comprise a solution or suspension that includes a solution with particles of the SSP $(Ph_3P)_2Cu(\mu\text{-}SePh)_2In(SePh)_2$ suspended therein. The SSP may be isolated by evaporation of by-product. Optionally, the isolated SSP may be re-crystallized in preparation for using the SSP to form the ternary chalcopyrite material $CuInSe_2$.

It will be apparent from the above description that, in additional embodiments, instead of using the same reagent (e.g., PhSeH) in each of the sequential additions to the reaction mixture, different reagents including different moieties (other than phenylselenol) may be added to the first solution to substitute different, selected moieties into the resulting SSP product at different selected locations within the structure of the SSP molecule or complex.

In accordance with yet further embodiments of the present invention, polymeric SSPs may be formed by polymerizing SSP molecules or complexes, such as the SSP molecules or complexes formed as previously described herein. For example, an organometallic polymeric SSP of the general formula $[L_2N(ER^1)_a(\mu\text{-}ER^2E)_bM'(ER^1)_c(ER^2E)_d]_m$ may be fabricated using Reactions 1 through 3 (which are the same as above and repeated below for convenience) and Reaction 12 below:

$$N-X + 2L \rightarrow L_2N-X \quad \text{Reaction 1}$$

$$L_2N-X + M'X_3 \rightarrow \tfrac{1}{2}\{L_2N(\mu\text{-}X)_2M'X_2\}_2 \quad \text{Reaction 2}$$

$$\tfrac{1}{2}\{L_2N(\mu\text{-}X)_2M'X_2\}_2 + 4MER \rightarrow L_2N(\mu\text{-}ER)_2M'(ER)_2 \\ (+4MX) \quad \text{Reaction 3}$$

$$L_2N(\mu\text{-}ER)_2M'(ER)_2 + n\,HE^1R^1E^1H \rightarrow [L_2N(ER)_a(\mu\text{-}E^1R^1E^1)_bM'(ER)_c(E^1R^1E^1)_d]_m \quad \text{Reaction 12}$$

wherein L is a Lewis base (that is coordinated to N by a dative bond), each N is individually selected from Group IB atoms, each M is individually selected from Group IA atoms, each M' is individually selected from Group IIIA atoms, each E is individually selected from Group VIA atoms, each $E^1$ is individually selected from Group VIA atoms (E and $E^1$ may be the same or different), each X is individually selected from group VIIA atoms or a nitrate group, n is any number from less than one (1) to four (4) or excess, a is any number from zero (0) to two (2), b is the difference between two (2) and a (b=2−a), c is any number from zero (0) to two (2), d is the difference between two (2) and c (d=2−c), the sum of b and d is equal to n (n=b+d) (if n is four (4) or less), m is any number representing the size of the resulting polymeric molecules or complexes, each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of α,ω-$E^1$ functionalized alkyl, vinyl, (per)fluoro alkyl, (per)fluoro aryl, silane, and carbamato groups.

In Reaction 12, up to four (4) units of the ER groups of the $L_2N(\mu\text{-}ER)_2M'(ER)_2$ substance may be replaced with E'R'E' to give linear or cross-linked polymeric SSPs. In other words, the degree of polymerization may be relatively higher when, for example, n is about four (4), and the degree of polymerization may be relatively lower when, for example, n is about one (1) or less, with intermediate degrees of polymerization being attained when n has an intermediate value between one (1) and four (4). It is noted that the $R^1$ groups in the four molar equivalents of the $HE^1R^1E^1H$ reagent may differ from one another, and may be individually selected from the group consisting of α,ω-$E^1$ functionalized alkyl, aryl, vinyl, (per)fluoro alkyl, (per)fluoro aryl, silane, and carbamato groups. It is noted that the $E^1$ groups in the four molar equivalents of the $HE^1R^1E^1H$ reagent may differ from one another, and may be individually selected from the Group VIA atoms.

In some embodiments, m may be one (1) or greater than one (1). For example, m may be between one (1) and about 20,000 or higher.

Reactions 1 through 3 may be carried out as previously described herein. Referring to Reaction 12, the non-polymeric organometallic substance $L_2N(\mu\text{-}ER)_2M'(ER)_2$ may be polymerized by reacting between about one (1) and about four (4) molar equivalents of $HE^1R^1E^1H$ with the $L_2N(\mu\text{-}ER)_2M'(ER)_2$ substance to form a polymeric organometallic SSP of the empirical formula $[L_2N(ER)_a(\mu\text{-}E^1R^1E^1)_bM'(ER)_c(E^1R^1E^1)_d]_m$. Reaction 12 may be carried out in a solution comprising benzene ($C_6H_6$) or a mixture of more than one solvent or another suitable solvent.

EXAMPLE 5

As a non-limiting example, one (1) molar equivalent of $(Ph_3P)_2Cu(\mu\text{-}SEt)_2In(SEt)_2$ (20.000 grams, 21.110 millimoles), which may be formed as previously described in Example 1, may be added to about 100 mL of benzene to form a first solution, which may be stirred. Four (4) molar equivalents of $HSCH_2CH_2SH(HSEtSH$, 7.0821 mL, 84.438 millimoles) may be added to the stirring first solution to form a first suspension including the product $[(Ph_3P)_2Cu(\mu\text{-}SCH_2CH_2S)_2In(SCH_2CH_2S)_2]_m$, where m may be between one (1) and about 20,000 or higher. The first suspension may be concentrated to form a solid product (or kept to continue the reaction as in a one pot reaction).

In some embodiments, two or more different SSPs (e.g., containing different N and/or M' atoms) may be polymerized by reacting between about one (1) and about four (4) or excess molar equivalents of $HE^1R^1E^1H$ with the two or more different SSPs to form copolymeric organometallic SSPs of the empirical formula $\{[L_2N^1(ER)_a(\mu\text{-}E^1R^1E^1)_bM'^1(ER)_c(E^1R^1E^1)_d]_m[L_2N^2(ER)_e(\mu\text{-}E^1R^1E^1)_fM'^2(ER)_g(E^1R^1E^1)_h]_n\}_l$, wherein L is a Lewis base coordinated to $N^1$ and $N^2$ by a dative bond, each $N^1$ and $N^2$ is individually selected from Group IB atoms ($N^1$ and $N^2$ may be the same or different), each $M'^1$ and $M'^2$ is individually selected from Group IIIA atoms ($M'^1$ and $M'^2$ may be the same or different), each E and $E^1$ is individually selected from Group VIA atoms (E and $E^1$ may be same or different), a is any number from zero (0) to two (2), b is the difference between two (2) and a (b=2−a), c is any number from zero (0) to two (2), d is the difference between two (2) and c (d=2−c), m is any number, e is any number from zero (0) to two (2), f is the difference between two (2) and e (f=2−e), g is any number from zero (0) to two (2), h is the difference between two (2) and g (h=2−g), n is any number, l is any number, each R group is individually selected from the group consisting of alkyl, aryl, vinyl, (per)fluoro alkyl, (per)fluoro aryl, silane, and carbamato groups, and each of the $R^1$ groups is individually selected from the group consisting of α,ω-$E^1$ functionalized alkyl, aryl, vinyl, (per)fluoro alkyl, (per)fluoro aryl, silane, and carbamato groups. It is noted that the $R^1$ groups in the four molar equivalents of the $HE^1R^1E^1H$ reagent may differ from one another, and may be individually selected from the group consisting of alkyl, aryl, vinyl, (per)fluoro alkyl, (per)fluoro aryl, silane, and carbamato groups. It is noted that the $E^1$ groups in the four molar equivalents of the $HE^1R^1E^1H$ reagent may be the same or different from one another, and may be individually selected from the Group VIA atoms. It is noted that all possible variations in identities and quantities of different SSPs can be used to form copolymeric single source precursors.

In some embodiments, m, n, and/may be one (1) or greater than one (1). For example, m, n, and/may be between one (1) and about 20,000 or higher (m, n, and l may be the same or different from one another).

EXAMPLE 6

As a non-limiting example, one (1) molar equivalent of $(Ph_3P)_2Cu(\mu\text{-}SEt)_2In(SEt)_2$ (10.000 grams, 10.555 millimoles) and one (1) molar equivalent of $(Ph_3P)_2Cu(\mu\text{-}SEt)_2Ga(SEt)_2$ (9.5240 grams, 10.555 millimoles), which may be provided using methods previously described herein, may be added to about 100 mL of benzene to form a first solution, which may be stirred. Eight (8) molar equivalents of $HSCH_2CH_2SH(HSEtSH$, 7.0821 mL, 84.438 millimoles) may be added to the stirring first solution to form a copolymeric, organometallic SSP having the empirical equation $\{[(Ph3P)_2Cu(\mu\text{-}SCH_2CH_2S)_2In(SCH_2CH_2S)_2]_m[(Ph_3P)_2Cu(\mu\text{-}SCH_2CH_2S)_2Ga(SCH_2CH_2S)_2]_n\}_l$, where m, n, and l may be between one (1) and about 20,000 or higher. The first suspension may be concentrated to form a solid product (or kept to continue the reaction as in a one pot reaction).

EXAMPLE 7

As a non-limiting example, one (1) molar equivalent of $(Ph_3P)_2Cu(\mu\text{-SEt})_2In(SEt)_2$ (10.000 grams, 10.555 millimoles), and one (1) molar equivalent of $(Ph_3P)_2Ag(\mu\text{-SEt})_2Ga(SEt)_2$ (9.9919 grams, 10.555 millimoles), which may be provided using methods previously described herein, may be added to about 100 mL of benzene to form a first solution, which may be stirred. Eight (8) molar equivalents of $HSCH_2CH_2SH(HSEtSH, 7.0821$ mL, 84.438 millimoles) may be added to the stirring first solution to form a copolymeric, organometallic SSP having the empirical formula $\{[(Ph_3P)_2Cu(\mu\text{-}SCH_2CH_2S)_2In(SCH_2CH_2S)_2]_m[(Ph_3P)_2Ag(\mu\text{-}SCH_2CH_2S)_2Ga(SCH_2CH_2S)_2]_n\}_l$, where m, n, and l may be between one (1) and about 20,000 or higher. The first suspension may be concentrated to form a solid product (or kept to continue the reaction as in a one pot reaction).

In accordance with some embodiments of the present invention, a copolymeric, organometallic SSP may be formed using methods described herein that includes two or more Group I metals, two or more Group III metals, and/or two or more Group VIA elements. For example, an SSP having the following formula may be formed in accordance with some embodiments of the present invention: $\{[(Ph_3P)_2Cu(\mu\text{-}SCH_2CH_2S)_2In(SCH_2CH_2S)_{2\text{-}}]_m[(Ph_3P)_2Cu(\mu\text{-}SCH_2CH_2S)_2Ga(SCH_2CH_2S)_2]_m[(Ph_3P)_2Cu(\mu\text{-}SCH_2CH_2S)_2Al(SCH_2CH_2S)_{2\text{-}}]_m[(Ph_3P)_2Ag(\mu\text{-}SCH_2CH_2S)_2In(SCH_2CH_2S)_{2\text{-}}]_m[(Ph_3P)_2Ag(\mu\text{-}SCH_2CH_2S)_2Ga(SCH_2CH_2S)_{2\text{-}}]_m[(Ph_3P)_2Ag(\mu\text{-}SCH_2CH_2S)_2Al(SCH_2CH_2S)_2]_m\}_m$, wherein each m may be between one (1) and about 20,000 or higher.

In some embodiments, two or more different $HE^1R^1E^1H$ species may be reacted with one or more than one $L_2N(\mu\text{-}ER)_2M'(ER)_2$ species in a polymerization reaction to form a copolymeric organometallic SSP having the empirical formula $\{[L_2N^1(\mu\text{-}ER)_a(\mu\text{-}E^1R^1E^1)_bM'^1(ER)_c(E^1R^1E^1)_d]_m[L_2N^2(\mu\text{-}ER)_e(\mu\text{-}E^1R^1E^1)_fM'^2(ER)_g(E^1R^1E^1)_h]_n\}_l$.

In some embodiments, one or more different $HE^1R^1E^1H$ species and one or more different $HE^2R^2$ species may be reacted with one or more different $L_2N(\mu\text{-}ER)_2M'(ER)_2$ species to form a polymeric organometallic SSP of the empirical formula $\{[L_2N(E^2R^2)_a(\mu\text{-}E^1R^1E^1)_bM'(E^2R^2)_c(E^1R^1E^1)_d]_m$. It is noted that the E, $E^1$, and $E^2$ atoms in the reagents may be the same or different, and may be individually selected from the Group VIA atoms.

EXAMPLE 8

As a non-limiting example, one (1) molar equivalent of $(Ph_3P)_2Cu(\mu\text{-SEt})_2In(SEt)_2$ (10.000 grams, 10.555 millimoles), which may be provided using methods previously described herein, may be added to about 100 mL of benzene to form a first solution, which may be stirred. Four (4) molar equivalent of $C_6H_5SeH$ (PhSeH, 4.4837 mL, 42.220 millimoles) and one (1) molar equivalent of $HSCH_2CH_2SH$ (HSEtSH, 0.88530 mL, 10.555 millimoles) may be added to the stirring first solution to form copolymeric organometallic SSPs having the empirical formula $[(Ph_3P)_2Cu(\mu\text{-}SCH_2CH_2S)(\mu\text{-SePh})In(SePh)_2]_m$ or $[(Ph_3P)_2Cu(\mu\text{-SePh})_2In(SePh)(SCH_2CH_2S)]_m$, where m may be between one (1) and about 20,000 or higher. The first suspension may be concentrated to form a solid product (or kept to continue the reaction as in a one pot reaction).

In accordance with additional embodiments of the present invention, a polymeric SSP of the general formula $[L_2N(ER)_a(\mu\text{-}E^1R^1E^1)_bM'(ER)_c(E^1R^1E^1)_d]_m$ may be fabricated using Reactions 1 and 2 (which are the same as above and repeated below for convenience), and additional Reaction 13 below:

N—X+2L→L$_2$N—X                    Reaction 1

L$_2$N—X+M'X$_3$→½{L$_2$N(μ-X)$_2$M'X$_2$}$_2$      Reaction 2

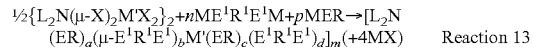
½{L$_2$N(μ-X)$_2$M'X$_2$}$_2$+nME$^1$R$^1$E$^1$M+pMER→[L$_2$N(ER)$_a$(μ-E$^1$R$^1$E$^1$)$_b$M'(ER)$_c$(E$^1$R$^1$E$^1$)$_d$]$_m$(+4MX)   Reaction 13 wherein L is a Lewis base that is coordinated to N by a dative bond, each N is individually selected from Group IB atoms, each M is individually selected from Group IA atoms, each M' is individually selected from Group IIIA atoms, each X is individually selected from Group VIIA atoms or a nitrate group, each E and $E^1$ is individually selected from Group VIA atoms (E and $E^1$ may be the same or different), n is any number from one (1) to four (4), p is the difference between four (4) and n (p=4−n), a is any number from zero (0) to two (2), b is the difference between two (2) and a (b=2−a), c is any number from zero (0) to two (2), d is the difference between two (2) and c (d=2−c), the sum of b and d is equal to n (n=b+d), the sum of a and c is equal top (p=a+c), m is any number representing the size of the resulting polymeric molecules or complexes, each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of α,ω-$E^1$ functionalized alkyl, aryl, vinyl, (per)fluoro alkyl, (per)fluoro aryl, silane, and carbamato groups. In some embodiments, m may be one (1) or greater than one (1). For example, m may be between one (1) and about 20,000 or greater.

Reactions 1 and 2 may be carried out as previously described herein. Referring to Reaction 13, the non-polymeric organometallic substance $L_2N(\mu\text{-}X)_2M'(X)_2$ may be polymerized by reacting between about one (1) and about four (4) molar equivalents of $ME^1R^1E^1M$ and MER (either sequentially or simultaneously) with the $L_2N(\mu\text{-}X)_2M'(X)_2$ substance to form a polymeric organometallic SSP of the empirical formula $[L_2N(ER)_a(\mu\text{-}E^1R^1E^1)_bM'(ER)_c(E^1R^1E^1)_d]_m$. Reaction 13 may be carried out in a solution comprising benzene $(C_6H_6)$ or another suitable solvent or solvent mixture.

EXAMPLE 9

As a non-limiting example, one (1) molar equivalent of $\frac{1}{2}\{(Ph_3P)_2Cu(\mu\text{-Cl})_2In(Cl)_2\}_2$ (67.635 grams, 80.064 millimoles), which may be provided using methods previously described herein, may be added to a mixture of about 240 mL of anhydrous benzene and 240 mL of anhydrous THF to form a first solution, which may be stirred. About two (2) molar equivalents of $NaSCH_2CH_2SNa$ (22.123 grams, 160.128 millimoles) and about two (2) molar equivalents of NaSEt (13.470 mL, 160.128 millimoles) may be added to the stirring first solution to form a polymeric, organometallic SSP having the empirical formula $[(Ph_3P)_2Cu(\mu\text{-}(SCH_2CH_2S))(\mu\text{-SEt})In(SCH_2CH_2S)(SEt)]_m$, where m may be between one (1) and about 20,000 or higher.

In some embodiments, two or more different $L_2N(\mu\text{-}X)_2M'(X)_2$ species may be polymerized by reacting between about one (1) and about four (4) molar equivalents of $ME^1R^1E^1M$ and MER (either sequentially or simultaneously) with the two or more different $L_2N(\mu\text{-}X)_2M'(X)_2$ species to form a copolymeric organometallic SSP of the empirical formula $\{[L_2N^1(ER)_a(\mu\text{-}E^1R^1E^1)_bM'^1(ER)_c(E^1R^1E^1)_d]_m[L_2N^2(ER)_e(\mu\text{-}E^1R^1E^1)_fM'^2(ER)_g(E^1R^1E^1)_h]_n\}_l$, wherein L is a Lewis base that is coordinated to $N^1$ and $N^2$ by dative bonds, each $N^1$ and $N^2$ is individually selected from Group IB atoms ($N^1$ and $N^2$ may be the same or different), each M is individually selected from Group IA atoms, each $M'^1$ and $M'^2$ is individually selected from Group IIIA atoms ($M'^1$ and $M'^2$ may be the same or different), each E and $E^1$ is individually selected from Group VIA atoms (E and $E^1$ may be the same or different), each X is individually selected from Group VIIA atoms or a nitrate group, a is any number from zero (0) to two (2), b is the difference between two (2) and a (b=2−a), c is any number from zero (0) to two (2), d is the difference between two (2) and c (d=2−c), m is any number, e is any number from zero (0) to two (2), f is the difference between two (2) and e (f=2−e), g is any number from zero (0) to two (2), h is the difference between two (2) and g (h=2−g), n is any number, l is any number, each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of α,ω-$E^1$ functionalized alkyl, aryl, vinyl, (per)fluoro alkyl, (per)fluoro aryl, silane, and carbamato groups. It is noted that the $E^1$ groups in the four molar equivalents of the $ME^1R^1E^1M$ reagent may differ from one another, and may be individually selected from the Group VIA atoms. It is noted that all possible variations in identities and quantities of any organometallic substance can be used to form copolymeric single source precursors. In some embodiments, m, n, and/may be one (1) or greater than one (1). For example, m, n, and/may be between one (1) and about 20,000 or higher (m, n, and/may be the same or different).

EXAMPLE 10

As a non-limiting example, one (1) molar equivalent of ½{(Ph$_3$P)$_2$Cu(μ-Cl)$_2$In(Cl)$_2$}$_2$ (33.818 grams, 40.032 millimoles) and one (1) molar equivalent of ½{(Ph$_3$P)$_2$Cu(μ-Cl)$_2$Ga(Cl)$_2$}$_2$ (32.012 grams, 40.032 millimoles), which may be formed using methods previously describe herein, may be added to a mixture of about 240 mL of anhydrous benzene and 240 mL of anhydrous THF to form a first solution, which may be stirred. About two (2) molar equivalents of NaSCH$_2$CH$_2$SNa (22.123 grams, 160.128 millimoles) and about two (2) molar equivalents of NaSEt (13.470 mL, 160.128 millimoles) may be added to the stirring first solution to form a copolymeric, organometallic SSP having the empirical equation {[(Ph$_3$P)$_2$Cu(μ-(SCH$_2$CH$_2$S))(μ-SEt)In(SCH$_2$CH$_2$S)(SEt)]$_m$[(Ph$_3$P)$_2$Cu(μ-(SCH$_2$CH$_2$S))(μ-SEt)Ga(SCH$_2$CH$_2$S)(SEt)]$_n$}$_l$, where m, n, and l may be between one (1) and about 20,000 or higher. The first suspension may be concentrated to form a solid product (or kept to continue the reaction as one pot reaction).

EXAMPLE 11

As a non-limiting example, one (1) molar equivalent of ½{(Ph$_3$P)$_2$Cu(μ-Cl)$_2$In(Cl)$_2$}$_2$ (33.818 grams, 40.032 millimoles) and one (1) molar equivalent of ½{(Ph$_3$P)$_2$Cu(μ-Cl)$_2$Ga(Cl)$_2$}$_2$ (32.012 grams, 40.032 millimoles), which may be provided using methods previous described herein, may be added to a mixture of about 240 mL of anhydrous benzene and 240 mL of anhydrous THF to form a first solution, which may be stirred. About four (4) molar equivalents of NaSCH$_2$CH$_2$SNa (NaSEtSNa, 44.246 grams, 320.256 millimoles) may be added to the stirring first solution to form a copolymeric, organometallic SSP having the empirical formula {[(Ph$_3$P)$_2$Cu(μ-(SEtS))$_2$In(SEtS)$_2$]$_m$[(Ph$_3$P)$_2$Cu(μ-(SEtS))$_2$Ga(SEtS)$_2$]$_n$}$_l$, where m, n, and l may be between one (1) and about 20,000 or higher. The first suspension may be concentrated to form a solid product (or kept to continue the reaction as a one pot reaction).

In some embodiments, two or more different $ME^1R^1E^1M$ and MER species may be polymerized by reacting between one or more than one of the $L_2N(\mu\text{-}X)_2M'(X)_2$ species to form a copolymeric organometallic SSP of the empirical formula $\{[L_2N^1(ER)_a(\mu\text{-}E^1R^1E^1)_bM'^1(ER)_c(E^1R^1E^1)_d]_m[L_2N^2(ER)_e(\mu\text{-}E^1R^1E^1)_fM'^2(ER)_g(E^1R^1E^1)_h]_n\}_l$.

Using the polymerization reactions described above, new polymeric, organometallic SSPs having the empirical formula $[L_2N(ER)_a(\mu\text{-}E^1R^1E^1)_bM'(ER)_c(E^1R^1E^1)_d]_m$ may be provided, wherein each of a, b, c, and d are between zero (0) and two (2). For example, in some embodiments, the SSPs may have the empirical formula $[L_2N(\mu\text{-}ER)(\mu\text{-}E^1R^1E^1)M'(ER)_c(E^1R^1E^1)_d]_m$. In additional embodiments, the SSPs may have the empirical formula $[L_2N(\mu\text{-}E^1R^1E^1)_2M'(ER)_c(E^1R^1E^1)_d]_m$. In additional embodiments, the SSPs may have the empirical formula $[L_2N(ER)_a(\mu\text{-}E^1R^1E^1)_bM'(ER)(E^1R^1E^1)]_m$. In yet further embodiments, the SSPs may have the empirical formula $[L_2N(ER)_a(\mu\text{-}E^1R^1E^1)_bM'(E^1R^1E^1)_2]_m$.

In some embodiments, the polymeric, organometallic SSPs may comprise substantially linear polymeric molecules or complexes. In additional embodiments, the polymeric, organometallic SSPs may comprise cross-linked substantially linear polymeric molecules or complexes. In yet further embodiments, the cross-linking between the individual SSP molecules or complexes may be so extensive that the polymeric, organometallic SSPs have a three-dimensional network structure.

The reaction pathways disclosed herein for forming SSPs allow the different R groups in the SSPs, as well as the different E, N, and M' atoms, to be selectively and individually tailored, which further allows chemical and physical properties of the SSPs, such as, for example, reactivity, solubility, melting point, boiling point, etc., to be selectively tailored.

SSPs (including polymeric SSPs and non-polymeric SSPs) made in accordance with embodiments of the present invention may be used to form chalocogenide materials (e.g., semiconductive ternary chalcopyrite materials) using methods such as, for example, those disclosed in U.S. patent application Ser. No. 12/047,956, filed Mar. 13, 2008, now U.S. Pat. No. 8,003,070, issued Aug. 23, 2011 to Fox et al., the disclosure of which is incorporated herein in its entirety by this reference.

Semiconductor materials and particles fabricated using SSPs formulated in accordance with embodiments of methods of the present invention may be used in many different types of semiconductor devices. For example, semiconductor materials and particles formed using embodiments of methods of the present invention may be used in semiconductor devices such as, for example, diodes (e.g., light emitting diodes (LEDs)), photovoltaic devices, sensors, solid state lasers, and integrated circuits (e.g., memory modules and microprocessors).

While the invention may be susceptible to various modifications and alternative forms, specific embodiments have been shown by way of example and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

What is claimed is:

1. A method of forming a polymeric single source precursor, comprising reacting $HE^1R^1E^1H$ with a single source precursor having the empirical formula $L_2N(\mu\text{-}ER)_2M'(ER)_2$ to form a polymeric single source precursor having the empirical formula $[L_2N(ER)_a(\mu\text{-}E^1R^1E^1)_bM'(ER)_c(E^1R^1E^1)_d]_m$, wherein L is a Lewis base coordinated to N by a dative bond, each N is individually selected from Group IB atoms, each M' is individually selected from Group IIIA atoms, each E and $E^1$ is individually selected from Group VIA atoms, a is any number from zero (0) to two (2), b is the difference between two (2) and a, c is any number from zero (0) to two (2), d is the difference between two (2) and c, m is any number greater than zero (0), each of the R groups is individually selected from the group consisting of alkyl, aryl, vinyl, (per)fluoro alkyl, (per)fluoro aryl, silane, and carbamato groups, and each of the $R^1$ groups is individually selected from the group consisting of $\alpha,\omega\text{-}E^1$ functionalized alkyl, aryl, vinyl, (per)fluoro alkyl, (per)fluoro aryl, silane, and carbamato groups.

2. The method of claim 1, wherein m is between 1 and 20,000.

3. The method of claim 1, wherein reacting $HE^1R^1E^1H$ with the organometallic substance comprises reacting about four (4) molar equivalents of $HSCH_2CH_2SH$ with about one (1) molar equivalent of $(Ph_3P)_2Cu(\mu\text{-}SEt)_2In(SEt)_2$ to form a polymeric single source precursor having the empirical formula $[(Ph_3P)_2Cu(\mu\text{-}SCH_2CH_2S)_2In(SCH_2CH_2S)_2]_m$.

4. A method of forming a polymeric single source precursor, comprising reacting at least one of $HE^1R^1E^1H$ and $HE^2R^2$ with a single source precursor having the empirical formula $L_2N(\mu\text{-}ER)_2M'(ER)_2$ to form a polymeric single source precursor having the empirical formula $[L_2N(E^2R^2)_a(\mu\text{-}E^1R^1E^1)_bM'(E^2R^2)_c(E^1R^1E^1)_d]_m$, wherein L is a Lewis base coordinated to N by a dative bond, each N is individually selected from Group IB atoms, each M' is individually selected from Group IIIA atoms, each E, $E^1$, and $E^2$ is individually selected from Group VIA atoms, a is any number from zero (0) to two (2), b is the difference between two (2) and a, c is any number from zero (0) to two (2), d is the difference between two (2) and c, m is any number greater than zero (0), and each R and $R^2$ is individually selected from the group consisting of alkyl, aryl, vinyl, (per)fluoro alkyl, (per)fluoro aryl, silane, and carbamato groups, and each $R^1$ is individually selected from the group consisting of $\alpha, \omega\text{-}E^1$ functionalized alkyl, aryl, vinyl, (per)fluoro alkyl, (per)fluoro aryl, silane, and carbamato groups.

5. A method of forming a polymeric single source precursor, comprising reacting $nME^1R^1E^1M$ and pMER with a substance having the empirical formula $L_2N(\mu\text{-}X)_2M'(X)_2$ to form a polymeric single source precursor having the empirical formula $[L_2N(ER)_a(\mu\text{-}E^1R^1E^1)_bM'(ER)_c(E^1R^1E^1)_d]_m$, wherein L is a Lewis base that is coordinated to N, each M is individually selected from Group IA atoms, each N is individually selected from Group IB atoms, each M' is individually selected from Group IIIA atoms, each E and $E^1$ is individually selected from Group VIA atoms, each X is individually selected from Group VIIA atoms or a nitrate group, n is any number from zero (0) to four (4), p is the difference between four (4) and n, a is any number from zero (0) to two (2), b is the difference between two (2) and a, c is any number from zero (0) to two (2), d is the difference between two (2) and c, m is any number greater than zero (0), each R is individually selected from the group consisting of alkyl, aryl, vinyl, (per)fluoro alkyl, (per)fluoro aryl, silane, and carbamato groups, and each $R^1$ is individually selected from the group consisting of $\alpha\omega\text{-}E^1$ functionalized alkyl, aryl, vinyl, (per)fluoro alkyl, (per)fluoro aryl, silane, and carbamato groups.

6. The method of claim 5, wherein m is between one (1) and 20,000.

7. The method of claim 5, wherein reacting $nME^1R^1E^1M$ and pMER with the substance having the empirical formula $L_2N(\mu\text{-}X)_2M'(X)_2$ comprises reacting $NaSCH_2CH_2SNa$ and NaSEt with $\frac{1}{2}\{(Ph_3P)_2Cu(\mu\text{-}Cl)_2In(Cl)_2\}_2$ to form $[(Ph_3P)_2Cu(\mu\text{-}(SCH_2CH_2S))(\mu\text{-}SEt)In(SCH_2CH_2S)(SEt)]_m$.

8. A polymeric, organometallic single source precursor having the empirical formula $[L_2N(ER)_a(\mu\text{-}E^1R^1E^1)_bM'(ER)_c(E^1R^1E^1)_d]_m$, wherein L is a Lewis base, each N is individually selected from Group IB atoms, each M' is individually selected from Group IIIA atoms, each E and $E^1$ is individually selected from Group VIA atoms, a is any number from zero (0) to two (2), b is the difference between two (2) and a, c is any number from zero (0) to two (2), d is the difference between two (2) and c, m is any number greater than zero (0), each R is individually selected from the group consisting of alkyl, aryl, vinyl, (per)fluoro alkyl, (per)fluoro aryl, silane, and carbamato groups, and each $R^1$ is individually selected from the group consisting of $\alpha,\omega\text{-}E^1$ functionalized alkyl, aryl, vinyl, (per)fluoro alkyl, (per)fluoro aryl, silane, and carbamato groups.

9. The polymeric, organometallic single source precursor of claim 8, wherein the polymeric, organometallic single source precursor comprises $[(Ph_3P)_2Cu(SEt)_a(\mu\text{-}SCH_2CH_2S)_bIn(SEt)_c(SCH_2CH_2S)_d]_m$.

10. The polymeric, organometallic single source precursor of claim 8, wherein the single source precursor has the empirical formula $[L_2N(\mu\text{-}ER)(\mu\text{-}E^1R^1E^1)M'(ER)_c(E^1R^1E^1)_d]_m$.

11. The polymeric, organometallic single source precursor of claim 8, wherein the single source precursor has the empirical formula $[L_2N(\mu\text{-}E^1R^1E^1)_2M'(ER)_c(E^1R^1E^1)_d]_m$.

12. The polymeric, organometallic single source precursor of claim 8, wherein the single source precursor has the empirical formula $[L_2N(ER)_a(\mu\text{-}E^1R^1E^1)_bM'(ER)_c(E^1R^1E^1)_d]_m$.

13. The polymeric, organometallic single source precursor of claim 8, wherein the single source precursor has the empirical formula $[L_2N(ER)_a(\mu\text{-}E^1R^1E^1)_bM'(E^1R^1E^1)_2]_m$.

14. The polymeric, organometallic single source precursor of claim 8, wherein m is between one (1) and about 20,000.

15. A method of forming a single source precursor for use in forming a chalcogenide material, comprising:
forming a first single source precursor having the empirical formula $L_2N(\mu\text{-}E^1R^1)_2M'(E^1R^1)_2$; and
reacting $HE^2R^2$ with the first single source precursor to form a different second single source precursor having the empirical formula $L_2N(\mu\text{-}E^2R^2)_2M'(E^2R^2)_2$;
wherein L is a Lewis base coordinated to N by a dative bond, each N is individually selected from Group IB atoms, each M' is individually selected from Group IIIA atoms, each $E^1$ and $E^2$ is individually selected from Group VIA atoms, and each $R^1$ and $R^2$ group is individually selected from the group consisting of alkyl, aryl, vinyl, (per)fluoro alkyl, (per)fluoro aryl, silane, and carbamato groups.

16. The method of claim 15, further comprising selecting at least one $E^1$ to differ from at least one $E^2$.

17. The method of claim 15, further comprising selecting at least one $R^1$ group to differ from at least one $R^2$ group.

* * * * *

UNITED STATES PATENT AND TRADEMARK OFFICE
CERTIFICATE OF CORRECTION

PATENT NO. : 8,829,217 B2  
APPLICATION NO. : 13/659620  
DATED : September 9, 2014  
INVENTOR(S) : Robert V. Fox et al.

Page 1 of 1

It is certified that error appears in the above-identified patent and that said Letters Patent is hereby corrected as shown below:

In the claims:

| | | | |
|---|---|---|---|
| CLAIM 4, | COLUMN 29, | LINE 46, | change "$\alpha, \omega\text{-}E^1$" to --$\alpha,\omega\text{-}E^1$-- |
| CLAIM 5, | COLUMN 29, | LINE 52, | change "$M'(ER)_c,$" to --$M'(ER)_c$-- |
| CLAIM 5, | COLUMN 30, | LINE 3, | change "$\alpha\omega\text{-}E^1$" to --$\alpha,\omega\text{-}E^1$-- |

Signed and Sealed this  
Twenty-ninth Day of December, 2015

Michelle K. Lee  
*Director of the United States Patent and Trademark Office*